US012161705B2

(12) United States Patent
Eckardt et al.

(10) Patent No.: US 12,161,705 B2
(45) Date of Patent: Dec. 10, 2024

(54) CHIMERIC ANTIGEN RECEPTOR SPECIFIC FOR TUMOR CELLS

(71) Applicant: Miltenyi Biotec B.V. & Co. KG, Bergisch Gladbach (DE)

(72) Inventors: Dominik Eckardt, Bergisch Gladbach (DE); Andreas Bosio, Cologne (DE); Jutta Kollet, Bonn (DE); Olaf Hardt, Cologne (DE); Andrzej Dzionek, Overath (DE); Stefan Tomiuk, Cologne (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 599 days.

(21) Appl. No.: 16/833,707

(22) Filed: Mar. 30, 2020

(65) Prior Publication Data

US 2020/0282035 A1 Sep. 10, 2020

Related U.S. Application Data

(63) Continuation of application No. 15/785,476, filed on Oct. 17, 2017, now Pat. No. 10,617,720.

(30) Foreign Application Priority Data

Oct. 20, 2016 (EP) .................................... 16194708

(51) Int. Cl.

*A61K 39/00* (2006.01)
*A61K 35/17* (2015.01)
*A61K 47/65* (2017.01)
*A61P 35/00* (2006.01)
*C07K 14/705* (2006.01)
*C07K 14/725* (2006.01)

(52) U.S. Cl.

CPC ...... *A61K 39/001129* (2018.08); *A61K 35/17* (2013.01); *A61K 47/65* (2017.08); *A61P 35/00* (2018.01); *C07K 14/7051* (2013.01); *C07K 14/70517* (2013.01); *C07K 14/70521* (2013.01); *C07K 14/70596* (2013.01)

(58) Field of Classification Search

CPC ............ A61K 39/4631; A61K 39/4644; C07K 16/28

See application file for complete search history.

(56) References Cited

PUBLICATIONS

Strickland (2009, Journal of Pathology, 218:380-390).*
Roybal (2016, Cell, 164:770-779).*
Oh (2012, JGO, 23:274-281).*
Kollmorgen (2013, Molecular Oncology, 7:1141-1151).*
Ahn, 2015, Biomaterials, 39:23-30.*

* cited by examiner

*Primary Examiner* — Valarie E Bertoglio
(74) *Attorney, Agent, or Firm* — Jaquelin K. Spong

(57) ABSTRACT

The present invention is directed to ligand like a chimeric antigen receptor (CAR), comprising an antigen binding domain specific for one or more antigens selected from the group consisting of CLA, CD142, CD73, CD49c, CD66c, CD104, CD318 and TSPAN8; cell populations expressing such CARs and the use of the cell populations for cancer therapy.

2 Claims, 9 Drawing Sheets

Specification includes a Sequence Listing.

CHIMERIC ANTIGEN RECEPTOR SPECIFIC FOR TUMOR CELLS

CROSS REFERENCE TO RELATED APPLICATIONS

This US non-Provisional patent application is a continuation claiming priority to U.S. Ser. No. 15/785,486, filed Oct. 17, 2017, which in turn claims priority to EP 16194708.0 filed in the European Patent Convention on Oct. 20, 2016. Each of these prior applications is incorporated by reference in their entireties.

STATEMENT REGARDING FEDERALLY SPONSORED RESEARCH

Not applicable.

STATEMENT REGARDING MICROFICHE APPENDIX

Not applicable.

FIELD OF THE INVENTION

The present invention relates to the use of ligands comprising antigen binding domains specific for certain antigens, like chimeric antigen receptors (CAR) and/or engineered cells provided with such ligands for treatment of human cancer.

BACKGROUND

Cancer is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. There are over 200 different known cancers that affect humans. Whereas good treatment options are available for many cancer types, others still represent unmet medical needs.

The technology of chimeric antigen receptor (CAR) may provide a promising approach for adoptive cell immunotherapy for cancer. Commonly, CARs comprise a single chain fragment variable (scFv) of an antibody specific for a tumor associated antigen (TAA) coupled via hinge and transmembrane regions to cytoplasmic domains of T-cell signaling molecules. For example, well known lymphocyte activation moieties include a T-cell costimulatory (e.g. CD28, CD137, OX40, ICOS, and CD27) domain in tandem with a T-cell triggering (e.g. CD3ζ) moiety. The CAR-mediated adoptive immunotherapy allows CAR-grafted cells to directly recognize the TAAs on target tumor cells in a non-HLA-restricted manner.

Paramount for immunotherapy for cancer based on CAR is the selection of antigens specific for the respective tumor cells. Object of the invention was to provide such antigens specific for cancer cells, especially for pancreas cancer cells in order to engineer killer cells which then kill/lyse cancer cells without attacking non-tumor cells.

SUMMARY

It has been found that a distinct group of cell surface antigens is expressed on several human cancer cells, especially on human pancreas cancer cells, but not or to a lower level on non-malignant cells. Accordingly, these antigens (also referred to as "markers") can be used to identify and/or mark and/or destroy and/or disable escape mechanisms of such cancer cells via ligands that specifically bind to the markers.

Therefore, the invention relates to a ligand, comprising an antigen binding domain specific for one or more antigens characterized in that the ligand is a chimeric antigen receptor (CAR), comprising an antigen binding domain specific for one or more antigens selected from the group consisting of CLA, CD142, CD73, CD49c, CD66c, CD104, CD318 and TSPAN8.

Another object of the invention are methods of binding a cancer cell with a ligand comprising an antigen binding domain specific for one or more antigens selected from the group consisting of CLA, CD142, CD73, CD49c, CD66c, CD104, CD318 and TSPAN8.

The ligands as further disclosed may be an antibody or a CAR or an engineered cell expressing at least one such ligands.

Another objects of the invention are populations of engineered cells expressing at least one of said ligands, pharmaceutical compositions comprising the population of engineered cells and/or the use of the population of engineered cells or the pharmaceutical composition for treatment of human cancer.

DETAILED DESCRIPTION OF THE INVENTION

Figure 1:
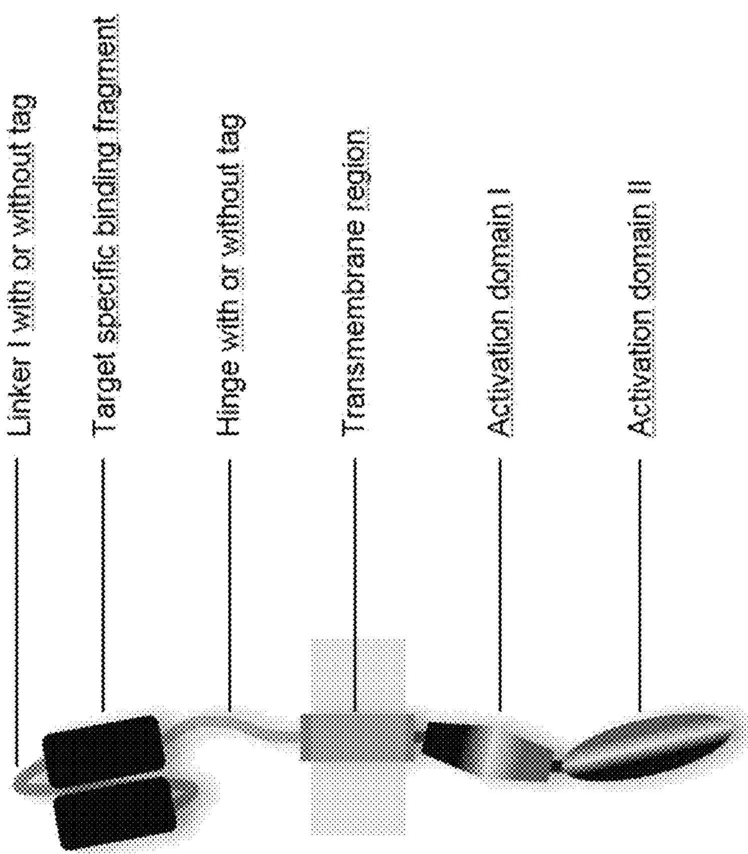
FIG. 1 shows the general structure of a CAR capable of recognizing a specific target.

In a first embodiment of the invention, the ligand comprises at least two different antigen binding domains specific for at least two different antigens selected from the group consisting of CLA, CD142, CD73, CD49c, CD66c, CD104, CD318 and TSPAN8. For example, the ligand may comprise antigen binding domains specific for CLA and CD66c or specific for CLA and TSPAN8.

In a preferred method of binding a cancer cell, the cancer cell (or population of cancer cells) is bound with a ligand comprised at least two different antigen binding domains specific for at least two different antigens selected from the group consisting of CLA, CD142, CD73, CD49c, CD66c, CD104, CD318 and TSPAN8. Again, the ligand may comprise antigen binding domains specific for CLA and CD66c or specific for CLA and TSPAN8.

Definitions

The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth. In cancer, cells (cancerous cells) divide and grow uncontrollably, forming malignant tumors, and invading nearby parts of the body. The cancer may also spread to more distant parts of the body through the lymphatic system or bloodstream.

The term "isolated" means altered or removed from the natural state. For example an isolated population of cells means an enrichment of such cells and separation from other cells which are normally associated in their naturally occurring state with said isolated cells. An isolated population of cells means a population of substantially purified cells which is a homogenous population of cells.

The terms "specifically binds" or "specific for" with respect to an antigen-binding domain of a ligand like an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refers to cells, preferentially T cells which are manipulated by recombinant methods well known in the art to express stably or transiently peptides or proteins which are not expressed in these cells in the natural state. For example, T cells are engineered to express an artificial construct such as a chimeric antigen receptor on their cell surface. For example, the sequences encoding the CAR may be delivered into cells using a retroviral or lentiviral vector.

The amino acid sequences given in SEQ ID NO: 1-32, respectively (in the one-letter code of amino acids) shall refer to all constellations of the respective amino acid sequence which retains the intended function of the respective amino acid sequence as defined. Therefore, all variants of the amino acid sequences defined in the sequence listings having a sequence identity of at least 70%, or at least 75%, 80%, 85%, 90%, 95%, 97%, 98% or 99% at the amino acid sequence level are included in the scope of the present invention. In the context of the present invention, "sequence identity" may be determined using pairwise alignments using alignments programs for amino acid sequences well known to the art.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as $CD4^+$ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, Th9, or $T_{FH}$, which secrete different cytokines to trigger a different type of immune response. Signaling from the APC directs T cells into particular subtypes.

Cytotoxic T cells ($T_C$ cells, or CTLs) destroy infected cells and tumor cells, and are also implicated in transplant rejection. These cells are also known as $CD8^+$ T cells since they express the CD8 glycoprotein at their surface. These cells recognize their targets by binding to antigen associated with MHC class I molecules, which are present on the surface of all nucleated cells.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells ($T_{CM}$ cells) and two types of effector memory T cells ($T_{EM}$ cells and $T_{EMRA}$ cells). Memory cells may be either $CD4^+$ or $CD8^+$. Memory T cells typically express the cell surface molecule CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of $CD4^+$ $T_{reg}$ cells have been described—Foxp3+ $T_{reg}$ cells and Foxp3− $T_{reg}$ cells.

Natural killer T cells (NKT cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both $T_h$ and $T_c$ cells (i.e., cytokine production and release of cytolytic/cell killing molecules).

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, such as T cell-based cytotoxic responses to attack cancer cells. T cells that have a natural or genetically engineered reactivity to a patient's cancer are generated in vitro and then transferred back into the cancer patient.

The term "biomarker" or "marker" is widespread in the art and may broadly denote a biological molecule and/or a detectable portion thereof (e.g. a nucleic acid, a peptide or a lipid such as a glycolipid) whose qualitative and/or quantitative evaluation in an individual is predictive or informative (e.g., predictive, diagnostic and/or prognostic) with respect to one or more aspects of the individual's phenotype and/or genotype. E.g. the biomarker is predictive or informative with respect to the outcome for chemotherapeutic treatment of a cancer in an individual. A biomarker is expressed ("expression of the biomarker") if the biomarker is detectable with methods known in the art. Therefore expression of biomarkers encompasses not only expression at nucleic acid level (DNA and/or RNA) and protein level but also expression (presence) of other biological structures on or in the cells such as glycolipids or the activity of a protein.

The term "target" as used herein refers to an antigen or epitope associated with a cell that should be recognized specifically by an antigen binding domain, e.g. an antigen binding domain of an antibody or of a CAR. The antigen or epitope for antibody recognition can be bound to the cell surface but also be secreted, part of the extracellular membrane, or shed from the cell.

The term "antibody" as used herein refers to polyclonal or monoclonal antibodies and fragments thereof, which can be generated by methods well known to the person skilled in the art. The antibody may be of any species, e.g. mice, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "killer cell" as used herein refers to a cell that can kill/lyse another cell, e.g. a cancer cell. Most frequently, T cells, NK cells, dendritic cells and macrophages can be used as killer cells.

The term "engineered killer cell" as used herein refers to a killer cell that is genetically modified to allow for the specific killing of a target cell, e.g. a cell modified with a CAR against a target to kill tumor cell expressing the respective target.

Chimeric Antigen Receptor (CAR)

The chimeric antigen receptor (CAR) according to the invention may comprise an antigen binding domain conjugated to a transmembrane domain and/or a intracellular signaling domain, as shown by way of example in FIG. 1.

In a first embodiment of the invention, the ligand is a chimeric antigen receptor (CAR), comprising an antigen binding domain specific for one or more antigens selected from the group consisting of CLA, CD142, CD73, CD49c, CD66c, CD104, CD318 and TSPAN8.

In a second embodiment of the invention, the ligand is a CAR, comprising an antigen binding domain specific for CLA in combination with one or more antigens selected from the group consisting of CD142, CD73, CD49c, CD66c, CD104, CD318 and TSPAN8.

In a third embodiment of the invention, the ligand is a CAR, comprising an antigen binding domain, an transmembrane domain and/or an intracellular signaling domain and comprising at least two antigen binding domains specific for two different antigens selected from the group consisting of CLA, CD142, CD73, CD49c, CD66c, CD104, CD318 and TSPAN8 are conjugated to the same or a different transmembrane domain and/or intracellular signaling domain.

In another embodiment of the invention, the antigen binding domain of a CAR binds a hapten that is coupled to a polypeptide ("haptenylated" polypeptide), wherein the polypeptide may bind to a tumor associated antigen. Such CARs are for example disclosed in U.S. Pat. No. 9,233,125B2 and are known in the art as "anti-tag" CAR. Similar, the extracellular part of the CAR of the invention may comprise a linker/label epitope (LLE) binding domain as antigen binding domain that binds to a linker/label epitope (LLE) that is part of a target cell binding molecule Such "anti-LLE CARs" are disclosed in the European patent application no. EP16196487.9. Both types of CARs are universal and/or adaptable CAR. Both the hapten(s) and the LLE are "tags" that are coupled directly or indirectly to a polypeptide (the tagged polypeptide), wherein the polypeptide may bind to a tumor associated antigen expressed on the (cell) surface of a target cell.

In this embodiment, the ligand comprises an antigen binding domain specific for one or more antigens characterized in that the ligand is a chimeric antigen receptor (CAR), comprising an anti tag binding region which can bind to a tag which is coupled to an antigen binding domain specific for one or more antigens selected from the group consisting of CLA, CD142, CD73, CD49c, CD66c, CD104, CD318 and TSPAN8. Suitable tags are for example, but not limited to, Biotin, other haptens, FITC or other fluorochrome molecules, FLAG, HIS, YOL MYC, Dextran, FcR, antibody-isotypes, artificially engineered epitopes, FAB or FAB2 binders.

The transmembrane domain of the CAR may comprise a sequence of the transmembrane domains of 4-1BB, CD8 and/or CD28; and the intracellular signaling domain comprises a sequence of the intracellular signaling domains of one or more of CD28, CD137 and CD3zeta.

In a preferred variant of this embodiment, the chimeric antigen receptor (CAR) comprises an antigen binding domain specific for CLA without an additional antigen binding domain or additional CAR, wherein the antigen binding domain is conjugated to one transmembrane domains and one or more signaling domains. This variant is shown by way of example in FIG. 2A.

In a second variant of the invention, the chimeric antigen receptor (CAR) comprises at least two antigen binding domains specific for two or more antigens selected from the group consisting of CLA (cutaneous lymphocyte antigen), CD142, CD73, CD49c, CD66c, CD104, CD318 and TSPAN8, wherein the antigen binding domains are conjugated to different transmembrane domains and/or signaling domains. This variant is shown by way of example in FIG. 2 b.

In a third variant of the invention, the chimeric antigen receptor (CAR) comprises at least two antigen binding domains specific for two or more antigens selected from the group consisting of CLA (cutaneous lymphocyte antigen), CD142, CD73, CD49c, CD66c, CD104, CD318 and TSPAN8, wherein the antigen binding domains are conjugated to the same (one) transmembrane domain and signaling domains. This variant is shown by way of example in FIG. 2 c.

In a forth variant of the invention, the chimeric antigen receptor (CAR) comprises at least two antigen binding domains specific for two or more antigens selected from the group consisting of CLA (cutaneous lymphocyte antigen), CD142, CD73, CD49c, CD66c, CD104, CD318 and TSPAN8, wherein the antigen binding domains are conjugated to different transmembrane domains and signaling domains and the antigen binding domains origin from one vector. This variant is shown by way of example in FIG. 2 d.

CLA is the cutaneous lymphocyte-associated antigen (CLA), a specialized glycoform of P-selectin glycoprotein ligand-1 (PSGL-1). It serves as a ligand for selectins, including CD62E (ELAM-1) and CD62L (LECAM-1). CLA is a unique skin-homing receptor and is predominantly found on a minor subset of human T cells that infiltrate the skin. This post-translational modification of PSGL-1 is thought to serve as a mechanism to regulate tissue-specific homing of CD4+ and CD8+ memory/effector T cells from peripheral blood to the skin, which plays an essential role during many inflammatory and certain malignant skin diseases.

In peripheral blood, CLA is not only found on skin-homing memory/effector T cells, but is also found to be expressed on memory/effector B cells, NK cells, blood dendritic cells, and on monocytes. CLA is furthermore found on Langerhans cells in the skin.

In order to enhance the specific recognition of cancer cells, the chimeric antigen receptor (CAR) may comprise an antigen binding domain specific for CLA in combination with one or more (like two, three or four) antigens selected from the group consisting of CD142, CD73, CD49c, CD66c, CD104, CD318 and TSPAN8. Preferred combinations specific for pancreas cancer are CLA with TSPAN8 and CLA with CD66c.

The antigen binding domain of said CAR may comprise, for example, full length heavy chain, Fab fragments, single chain Fv (scFv) fragments, divalent single chain antibodies or diabodies, each of which are specific for one or more of the target antigens CLA, CD142, CD73, CD49c, CD66c, CD104, CD318 and TSPAN8.

The antigen binding domain of said CAR may comprise the amino acid sequences of SEQ ID NO:1 and SEQ ID NO:2. The relevant sites causing specificity for antigen binding are the CDRs according to the IMGT (the international ImMunoGeneTics information system for immunoglobulins or antibodies) definition which are underlined in the sequence. The antigen binding domain of said CAR may comprise a scFv comprising the amino acid sequence of SEQ ID NO:17 or SEQ ID NO:18.

The present invention also encompasses nucleic acids (DNA or RNA) constructs comprising sequences encoding for amino acids sequences of a CAR specific for the disclosed markers.

In one embodiment of the invention a DNA construct (vector, plasmid) is generated encoding for a CAR specific for the disclosed markers. A nucleic acid sequence encoding for an antigen binding domain specific for the disclosed markers is fused at least to a nucleic acid sequence encoding a transmembrane domain and subsequent a nucleic acid sequence encoding a intracellular domain. The construction of such expression vectors can be performed by recombinant methods well known in the art. Alternatively, the nucleic acid sequences can be produced synthetically.

Alternatively, the CAR may be composed of further parts such as a linker and/or hinge and/or may be composed as di- or multi-chain CAR as described below.

Figure 2:
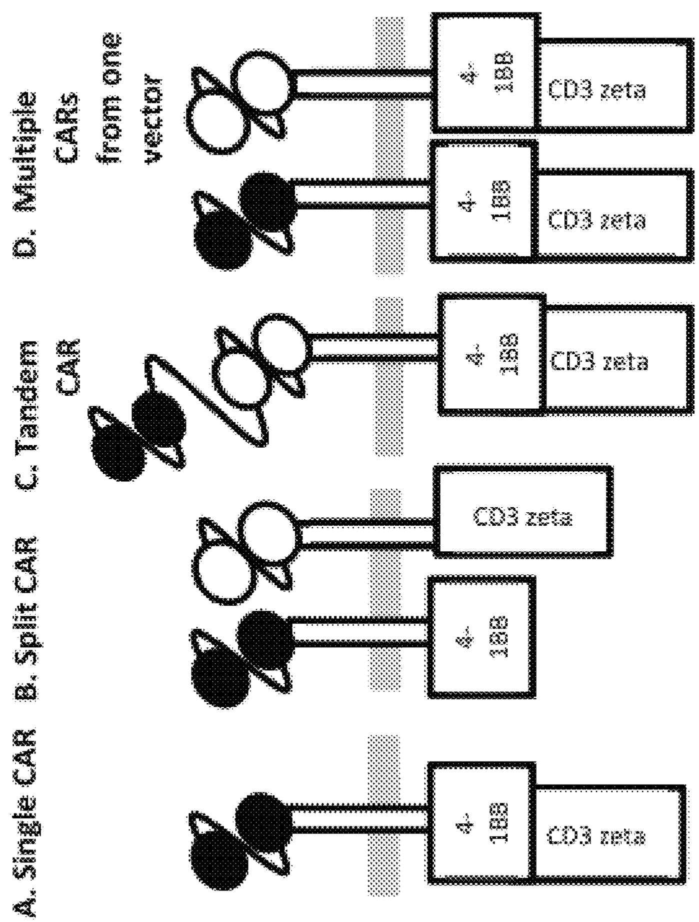
FIG. 2 shows the variants of CAR.

As shown in general in FIGS. 1 and 2, a CAR may comprise an extracellular domain comprising the antigen binding domain, a transmembrane domain and an intracellular signaling domain. The extracellular domain may be linked to the transmembrane domain by a linker. The extracellular domain may also be linked to a signal peptide.

A "signal peptide" refers to a peptide sequence that directs the transport and localization of the protein within a cell, e.g. to a certain cell organelle (such as the endoplasmic reticulum) and/or the cell surface.

An "antigen binding domain" refers to the region of the CAR that specifically binds to an antigen (and thereby is able to target a cell containing an antigen). The CARs of the invention may comprise one or more antigen binding domains. Generally, the antigen binding domain on the CAR are extracellular. The antigen binding domain may comprise an antibody or a fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors can be used as an antigen binding domain. Often the antigen binding domain is a scFv. Normally, in a scFv the variable portions of an immunoglobulin heavy chain and light chain are fused by a flexible linker to form a scFv. Such a linker may be for example the "$(G_4/S_1)_3$-linker".

In some instances, it is beneficial for the antigen binding domain to be derived from the same species in which the CAR will be used in. For example, if it is planned to use it therapeutically in humans, it may be beneficial for the antigen binding domain of the CAR to comprise a human or humanized antibody or fragment thereof. Human or humanized antibodies or fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to pass such a spacer. The spacer may include Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR can be derived from any desired natural or synthetic source for such domain. If the source is natural the domain may be derived from any membrane-bound or transmembrane protein. The transmembrane domain may be derived for example from CD8alpha or CD28.

The cytoplasmic domain or the intracellular signaling domain of the CAR of the invention is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR of the invention to perform a specialized function. The intracellular signaling domain may include any complete or truncated part of the intracellular signaling domain of a given protein sufficient to transduce the effector function signal.

Prominent examples of intracellular signaling domains for use in the CARs include the cytoplasmic sequences of the T cell receptor (TCR) and co-receptors that act in concert to initiate signal transduction following antigen receptor engagement.

Generally, T cell activation can be mediated by two distinct classes of cytoplasmic signaling sequence, firstly those that initiate antigen-dependent primary activation through the TCR (primary cytoplasmic signaling sequences) and secondly those that act in an antigen-independent manner to provide a secondary or co-stimulatory signal (secondary cytoplasmic signaling sequences).

Primary cytoplasmic signaling sequences that act in a stimulatory manner may contain ITAMs (immunoreceptor tyrosine-based activation motifs signaling motifs).

Examples of ITAM containing primary cytoplasmic signaling sequences often used in CARs derived from TCR zeta, FcR gamma, FcR beta, CD3 gamma, CD3 delta, CD3 epsilon, CD5, CD22, CD79a, CD79b, and CD66d.

The cytoplasmic domain of the CAR can be designed to comprise the CD3-zeta signaling domain by itself or combined with any other desired cytoplasmic domain(s). The cytoplasmic domain of the CAR can comprise a CD3 zeta chain portion and a costimulatory signaling region. The costimulatory signaling region refers to a part of the CAR comprising the intracellular domain of a costimulatory molecule. A costimulatory molecule is a cell surface molecule other than an antigen receptor or their ligands that is required for an efficient response of lymphocytes to an antigen. Examples for costimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3-zeta and the signaling domain of CD28. In another example the cytoplasmic domain may comprise the signaling domain of CD3-zeta and the signaling domain of CD27. In an further example, the cytoplasmic domain may comprise the signaling domain of CD3-zeta, the signaling domain of CD28, and the signaling domain of CD27.

The CAR of the invention may be designed to comprise any portion or part of the above-mentioned domains as described herein, especially in the variants shown in FIG. 2 a-d. The specificity of the CAR of the invention mediated by the antigen binding domain is for one or more of the antigens CLA, CD142, CD73, CD49c, CD66c, CD104, CD318 and TSPAN8 all other domains necessary to construct a functional CAR may be chosen from the options mentioned above or which are well known to the person skilled in the art.

Engineered Cells Expressing the Ligand

In another embodiment of the invention, the ligand is an engineered cell (or a population thereof), expressing at least one antigen binding domain specific for one or more antigens selected from the group consisting of CLA, CD142, CD73, CD49c, CD66c, CD104, CD318 and TSPAN8.

In a preferred embodiment, the population of engineered cells express an ligand like an chimeric antigen receptor (CAR) comprising an antigen binding domain specific for CLA in combination with one or more CARs and/or antigens selected from the group consisting of CD142, CD73, CD49c, CD66c, CD104, CD318 and TSPAN8.

The population of engineered cells may consist of T cells, macrophages or NK cells. The population of engineered cells may be are expanded to an therapeutically effective amount of cells before use in said immunotherapy.

To generate cells expressing the one or more CAR of the invention (including the variants), a DNA construct encoding the CAR of the invention can be transfected or transduced into a host cell by methods well known in the art (e.g. viral-based systems, physical methods, biological methods, chemical methods). Regardless of the methods used to integrate the nucleic acid encoding the CAR of the invention in the host cell, as a result the host cell expresses a CAR which is specific for the markers as disclosed.

In one embodiment of the invention, the engineered cells are isolated (enriched or separated) after the transfection/transduction process for generating such an engineered cell from non-transfected/transduced cells by methods well known in the art, e.g. fluorescent based separating technologies such as FACS® or magnetic cell separation methods such as MACS®.

In another embodiment of the invention a source of immune cells, preferentially T cells is obtained from a subject. Immune cells, preferentially T cells can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FACSsort) or magnetic sorting (e.g. MACS®).

For example, T cells of a blood sample of a subject are magnetically labelled, for example with a magnetic bead coupled to antibodies specific for CD4 and for CD8 or alternatively CD62L, respectively, washed, magnetically enriched and collected. Then these T cells may be engineered to express the antigens as disclosed or the preferred combination of antigens on their cell surface.

In one embodiment of the invention the isolated/enriched engineered T cells expressing an antigens as disclosed or the preferred combination of antigens prior or after genetic modification can be activated and expanded to increase amount of engineered T cells generally using methods well known in the art, for example polyclonal stimulation with anti-CD3/anti-CD28 beads or anti-CD3/anti-CD28 nanomatrices (as disclosed in EP2711418A1). Preferentially, said amount of engineered T cells is increased to a therapeutic effective amount.

In one embodiment of the invention a cell expressing the CAR of the invention is generated. The RNA encoding the CAR of the invention can be transfected or transduced into a host cell by methods well known in the art (e.g. viral-based systems, physical methods, biological methods, chemical methods). In general, such an "RNA-engineered cell" is disclosed in detail in WO2013/040557. Regardless of the methods used to integrate the RNA encoding the CAR of the invention in the host cell, as a result the host cell expresses a CAR which is specific for an antigen as disclosed or the preferred combination of antigens. Using "RNA-engineered cells" lead to the fact that the CAR is expressed for a limited time in the cell (transient expression).

In one embodiment of the invention, the engineered cells are generated automatically in a closed cell culture system. Such process may comprises the steps:

a) providing a cell sample
b) preparation of the cell sample by centrifugation
c) magnetic separation of the cell, preferentially T cells, T cell subsets or T cell progenitors
d) activation of the enriched cells, preferentially T cells, T cell subsets or T cell progenitors using modulatory agents
e) genetically modifying the cells, preferentially T cells, T cell subsets or T cell progenitors to express one or more CARs as disclosed or the preferred combination of CARs/antigens
f) expansion of the genetically modified T cells, T cell subsets or T cell progenitors in a cultivation chamber
g) washing of the cultured cells, preferentially T cells, T cell subsets or T cell progenitors.

All these steps may be performed in a closed and sterile system.

The process is especially suited for preparing gene modified cells, preferentially T cells, T cell subsets or T cell progenitors wherein the enriched cells, preferentially T cells, T cell subsets or T cell progenitors are gene modified by using viral and/or non-viral vectors. Any of these steps may be multiplied, omitted or may occur in a different order. In a variant of the invention, the modulatory agents are selected from agonistic antibodies and/or cytokines.

As closed and sterile system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes. It has been developed to fully automate and standardize the manufacturing process of cellular therapeutic agents. The instrument can perform sample loading, cell washing, density-based cell separations including erythrocyte reduction and plasma harvesting, magnetic separation, cell activation, cell modification (transduction), cell culture, and final product formulation.

Thus enabling the flexible integration of process modules ("steps") in a closed, automated and safe GMP compliant workflow reproducing a complex desired biological process.

In one embodiment of the invention, the genetically modified cells express one of the targets. To circumvent killing among the genetically modified cell population, this target is temporarily or permanently knocked down or knocked out on the killer cells. Temporal or permanent knock down or knock out of expression can be induced by methods well known in the art, such as siRNA for temporal knock down or the CRISPR system for permanent knock out. To inhibit target expression using these methods, this can be achieved by directly targeting the whole gene encoding for the target, parts of the gene, e.g. specific exons, the promotor region, or controlling genes, such as transcription factors. In the case of target structures representing glycostructures, such as CLA, this can also be achieved by altering the glycosylation site on the backbone protein or one or more of the enzymes catalyzing the glycosylation.

Methods of Use

Another embodiment of the invention is a method of binding a cancer cell with a ligand comprising at least two different antigen binding domains specific for at least two different antigens selected from the group consisting of CLA, CD142, CD73, CD49c, CD66c, CD104, CD318 and TSPAN8. In other words, the cancer cell is bound with a ligand comprising at two different antigen binding domains wherein a first antigen binding domain is specific for at least one antigen selected from the group consisting of CLA, CD142, CD73, CD49c, CD66c, CD104, CD318 and TSPAN8 and a second antigen binding domain is specific for at least one other antigen selected from the group consisting of CLA, CD142, CD73, CD49c, CD66c, CD104, CD318 and TSPAN8. Preferential combinations comprise CLA with CD66c and CLA with TSPAN8.

The ligands according to the invention may be used in combination with agents, which bind to the antigen and affect the viability of the cancerous cell expressing this antigen, preferentially kill the cancerous cell. Examples of such agents are oncolytic viruses, BiTEs®, ADCCs and immunotoxins.

An oncolytic virus is a virus that preferentially infects and kills cancer cells. As the infected cancer cells are destroyed by lysis, they release new infectious virus particles to help destroy the remaining tumor. Oncolytic viruses are thought not only to cause direct destruction of the tumor cells, but also to stimulate host anti-tumor immune responses. Specific targeting (e.g. targeting/ligation to the antigens as disclosed) involves modifying the viral coat proteins to target tumor cells (e.g. with antigen binding domain specific for antigens as disclosed) while reducing entry to non-tumor cells.

Bi-specific T-cell engagers (BiTEs®) are a class of artificial bispecific monoclonal antibodies that are investigated for the use as anti-cancer drugs. They direct a host's immune system, more specifically the T cells' cytotoxic activity, against cancer cells. BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule. Like other bispecific antibodies, and unlike ordinary monoclonal antibodies, BiTEs® form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

Antibody-dependent cell-mediated cytotoxicity (ADCC) is a mechanism of attack by the immune system that requires the presence of antibodies bound to the surface of target cells. Antibodies are formed of a binding region (Fab), which binds to the target antigen and the Fc region that can be detected by immune cells via Fc receptors on their surface. These Fc receptors are found on the surface of many cells of the immune system, including natural killer cells. When a natural killer cell encounter cells coated with antibodies, the Fc regions interact with their Fc receptors, leading to the release of perforin and granzyme B. These two chemicals lead to the tumor cell initiating programmed cell death (apoptosis). Antibodies known to induce this method of cell killing include Rituximab, Ofatumumab, Trastuzumab, Cetuximab and Alemtuzumab. Third generation antibodies that are currently being developed have altered Fc regions that have higher affinity for a specific type of Fc receptor, FcγRIIIA, which can increase the rate of ADCC dramatically.

An immunotoxin is a human-made protein that consists of a targeting portion linked to a toxin. When the protein binds to that cell, it is taken in through endocytosis, and the toxin kills the cell. These chimeric proteins are usually made of a modified antibody or antibody fragment, attached to a fragment of a toxin. The "targeting portion" is composed of the Fv portion of an antibody that binds specifically to an antigen expressed by a cell, preferably by a specific cell type. The toxin is usually a cytotoxic protein derived from a bacterial or plant protein, from which the natural binding domain has been removed so that the Fv directs the toxin to the antigen on the target cell.

Pharmaceutical Composition

Another object of the invention is a pharmaceutical composition comprising a population of engineered cells expressing a CAR as already disclosed, optionally with a pharmaceutical acceptable carrier like Composol or NaCl solution.

Use for Treatment of Cancer

The population of engineered cells as disclosed and/or the pharmaceutical composition comprising the population of engineered cells may be used in a method for treatment of human cancer with cells expressing the disclosed target molecules, especially of human pancreas cancer.

The pharmaceutical composition comprises preferable a population of engineered cells expressing a CAR. In a variant of the invention, the pharmaceutical composition is used in combination with a chemotherapeutic, radiation, or immunomodulatory agent for treatment of cancer.

The cancer to be treated may include hematopoietic cancer, myelodysplastic syndrome, pancreatic cancer, head and neck cancer, cutaneous tumors, minimal residual disease (MRD) in acute lymphoblastic leukemia (ALL), acute myeloid leukemia (AML), lung cancer, breast cancer, ovarian cancer, prostate cancer, colon cancer, melanoma or other hematological cancer and solid tumors, or any combination thereof. In another embodiment, the cancer includes a hematological cancer such as leukemia (e.g., chronic lymphocytic leukemia (CLL), acute lymphocytic leukemia (ALL), acute myeloid leukemia (AML), or chronic myelogenous leukemia (CML), lymphoma (e.g., mantle cell lymphoma, non-Hodgkin's lymphoma or Hodgkin's lymphoma) or multiple myeloma, or any combination thereof. Furthermore, the cancer may include an adult carcinoma comprising coral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

The treatment of cancer may encompass any method which involves at least one antigen as disclosed or any combination of antigens as disclosed as target molecule. Such methods may be e.g. treatment with agents which bind to the antigen and affect the viability of the cancerous cell expressing this antigen, preferentially kill the cancerous cell. Examples are oncolytic viruses, BiTEs®, ADCCs and immunotoxins as already disclosed.

For the treatment, immune cells, e.g. T cells of a subject may be isolated. The subject may suffer from said cancer or may be a healthy subject. These cells are genetically modified in vitro or in vivo to express one or more CARs of the invention. These engineered cells may be activated and expanded in vitro or in vivo. In a cellular therapy these engineered cells may be infused to a recipient in need thereof. These cells may be a pharmaceutical composition (said cell plus pharmaceutical acceptable carrier). The infused cells are able to kill (or at least stop growth of) cancerous cells expressing one or more of the disclosed antigens in the recipient. The recipient may be the same subject from which the cells was obtained (autologous cell therapy) or may be from another subject of the same species (allogeneic cell therapy).

In one embodiment of the invention the subject suffering from pancreas cancer may be treated with the pharmaceutical composition of the invention together with an immunomodulatory agent, such as but not limited to Rapamycin or agents blocking PD-1/PD-L1 or CTLA4 signaling.

In one embodiment of the invention, due to the fact that the cancerous cells expressing one or more of the disclosed antigens may be only a subpopulation of the cancerous cells of the subject the subject may be treated additionally with chemotherapy or radiotherapy. Chemotherapeutic and radiation agents suited to treat cancers are well known in the art.

In one embodiment of the invention the CAR expressing cells are applied to a subject suffering from cancer, especially pancreas cancer as cellular therapy as disclosed above but in combination with a second activating CAR, which is also expressed on the same engineered cells, recognizing an additional epitope on the cancerous cells expressing one or more of the disclosed antigens to increase the specificity of the engineered cells expressing both CARs. This epitope can be membrane bound, part of the extracellular matrix, or a soluble component.

In one embodiment of the invention the CAR expressing cells are applied to a subject suffering from cancer as cellular therapy as disclosed above but in combination with a second, inhibitory CAR, which is also expressed on the same engineered cells, recognizing an additional epitope to increase the specificity of the engineered cells expressing both CARs. This epitope can be membrane bound, part of the extracellular matrix, or a soluble component.

The immune cells, preferentially T cells engineered to express one or more of the disclosed antigens may be administered either alone, or as a pharmaceutical composition in combination with diluents and/or with other components such as IL-2 or other cytokines or cell populations. Briefly, pharmaceutical compositions of the present invention may comprise a cell population of genetically modified cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins;

polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

A pharmaceutical composition comprising the immune cells, preferentially T cells disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected directly into a tumor, lymph node, or site of infection.

EXAMPLES

The following examples are intended for a more detailed explanation of the invention but without restricting the invention to these examples.

Example 1: Expression of Targets on Pancreatic Cancer

Figure 3:
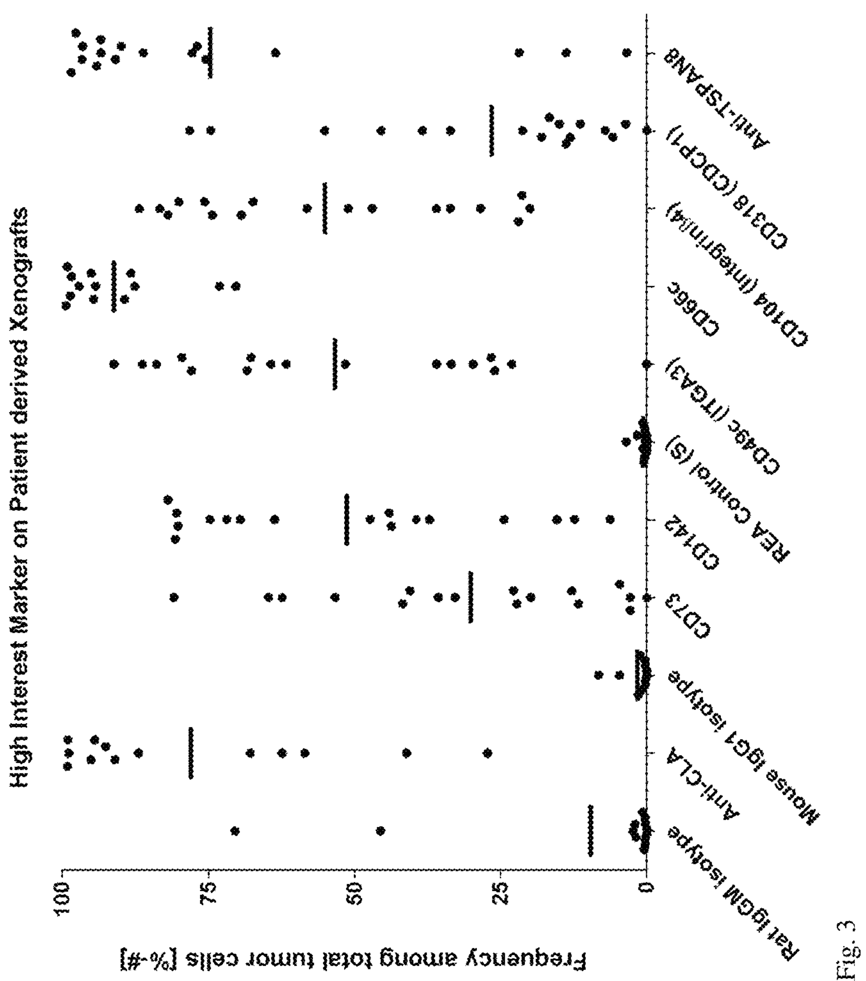
FIG. 3 shows the expression of CLA, CD142, CD73, CD49c, CD66c, CD104, CD318 and TSPAN8 on xenotransplanted human pancreatic cancer cells.
Figure 4:
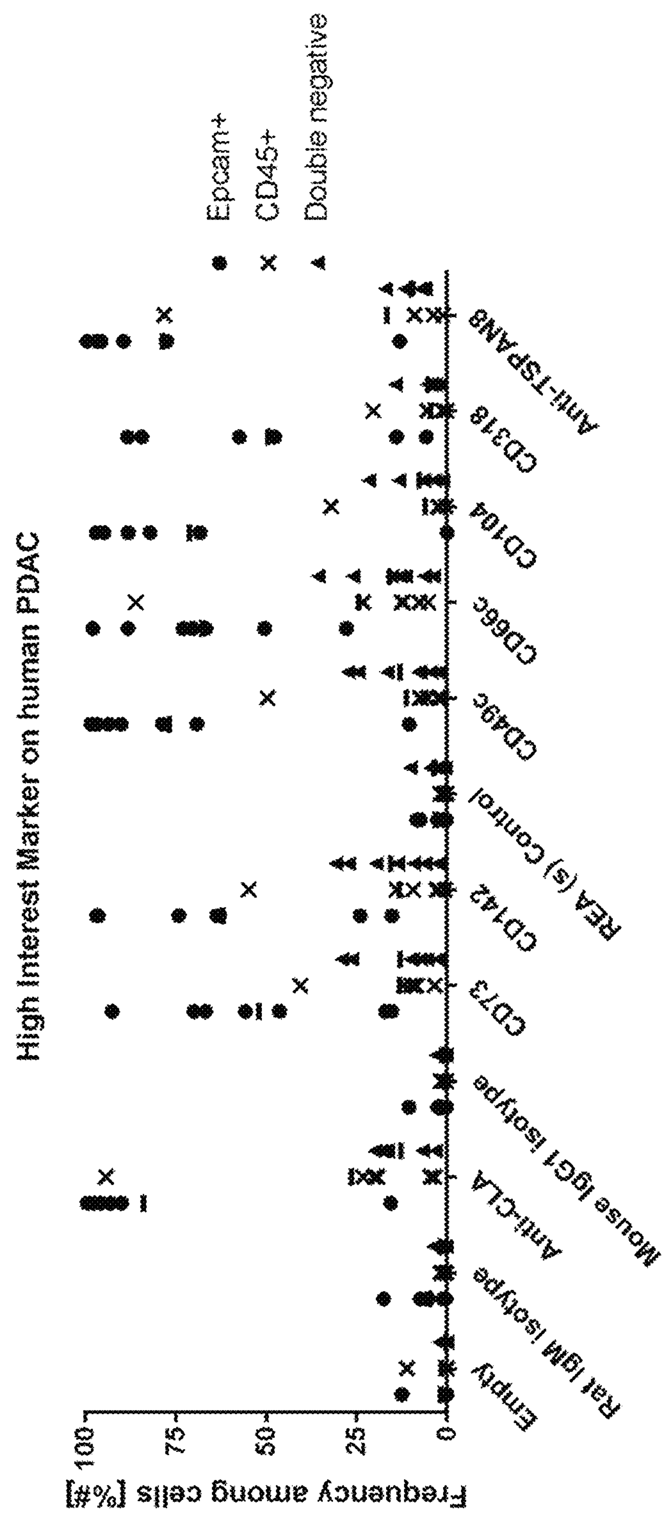
FIG. 4 shows the expression of CLA, CD142, CD73, CD49c, CD66c, CD104, CD318 and TSPAN8 on primary human pancreatic cancer cells and healthy tumor infiltrating cells.
Figure 5:
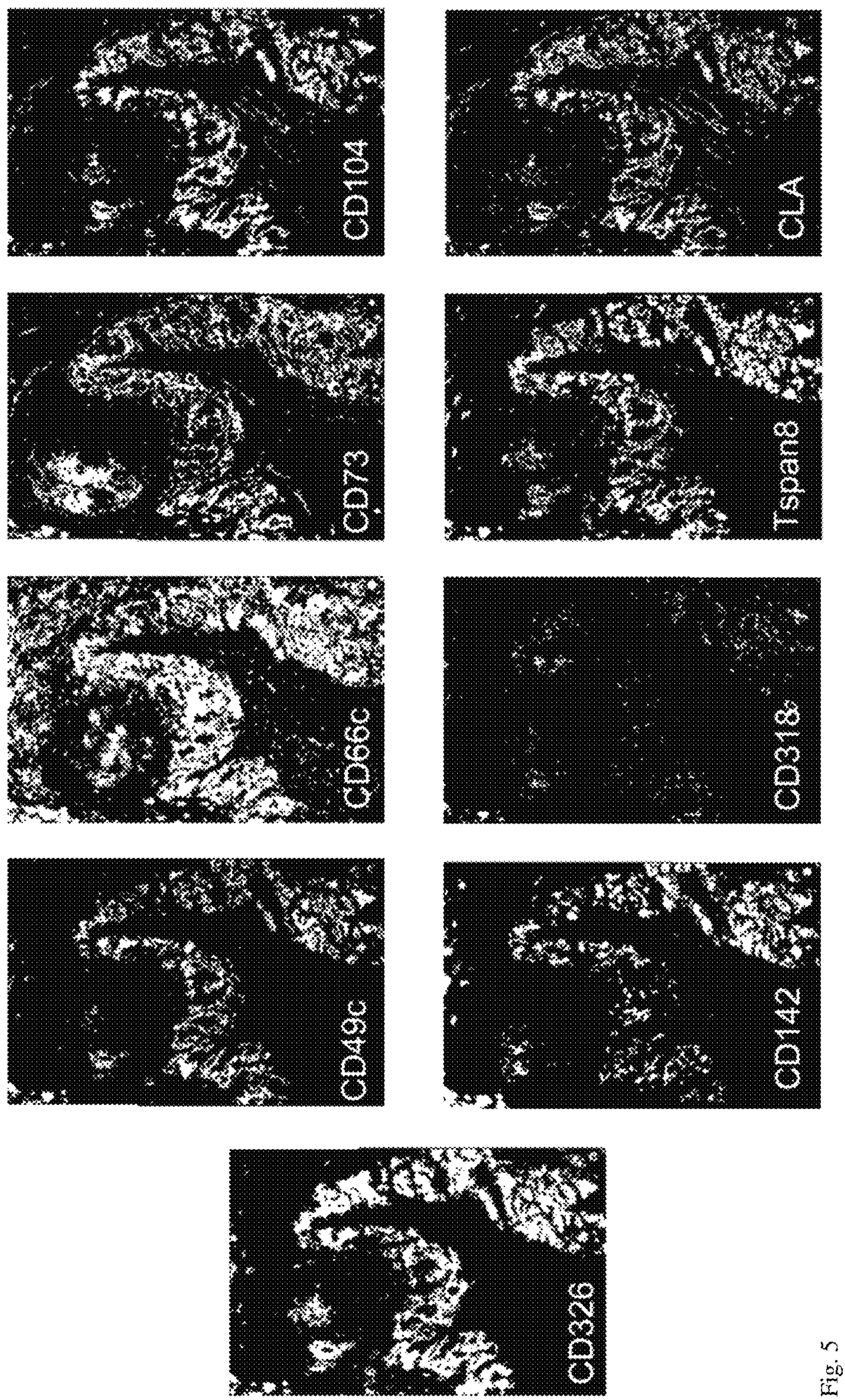
FIG. 5 shows the expression of CLA, CD142, CD73, CD49c, CD66c, CD104, CD318 and TSPAN8 on primary human pancreatic cancer sections.

Expression of CLA, CD142, CD73, CD49c, CD66c, CD104, CD318 and TSPAN8 on xenotransplanted human pancreatic cancer cells indicates the strong abundance of these markers on pancreatic cancer cells independent on the tumor microenvironment (FIG. 3). In addition, all markers are also reproducibly expressed at high levels on primary human pancreatic cancer cells (marked Epcam+) but neither on healthy tumor infiltrating leukocytes (marked CD45+) cells nor on other healthy tissue resident cell types (marked Double negative) (FIG. 4). These results were further validated using immunohistochemistry based detection of target expression in human pancreas cancer (FIG. 5).

Example 2: Structure of a CAR Recognizing Pancreas Cancer Specific Targets

The linkers used may comprise an epitope/tag allowing for the detection of the CAR as shown in FIG. 1. Examples for epitopes/tags are YOL, cMYC, or HIS. The pancreas cancer target specific binding fragment is derived from one or several antibodies specific for CLA, CD142, CD73, CD49c, CD66c, CD104, CD318 and/or TSPAN8. The hinge region may be derived e.g. from IgG domains, CD8a, or CD28 and may comprise an epitope/tag allowing for the detection of the CAR. The transmembrane domain may be derived e.g. from CD8a or CD28 followed by one to three signaling domains. These domains may be derived e.g. from CD28, 4-1BB, OX40, or CD3 zeta.

Example 3: Structure of Dual CAR Recognizing Pancreas Cancer Specific Targets

Recognition of two or more targets can be solved by either combining multiple antigen binding sites on one CAR molecule or by using multiple CAR molecules which are expressed in one cell and only work in combination, e.g. by using signaling domains for each of the CAR constructs that are inefficient for cell activation when used alone (FIG. 2).

Example 4: Amino Acid Sequence of the CLA Specific Antibody

The amino acid sequences of the variable portions of the immunoglobulin heavy chain and light chain of the used antibody specifically binding to CLA were as given in SEQ ID NO:1 and SEQ ID NO:2, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CLA can be used to generate a CAR recognizing CLA. The sequences given in SEQ ID NO:1 and SEQ ID NO:2 are only exemplary for sequences which are specific for the antigen CLA (the sequences are given in one letter code for amino acids). Other sequences may be used for generating antigen binding domains of an antibody or of a CAR which are also specific for the antigen CLA.

Example 5: Amino Acid Sequence of the CD142 Specific Antibody

The amino acid sequences of the variable portions of the immunoglobulin heavy chain and light chain of the used antibody specifically binding to CD142 were as given in SEQ ID NO:3 and SEQ ID NO:4, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD142 can be used to generate a CAR recognizing CD142. The sequences given in SEQ ID NO:3 and SEQ ID NO:4 are only exemplary for sequences which are specific for the antigen CD142 (the sequences are given in one letter code for amino acids). Other sequences may be used for generating antigen binding domains of an antibody or of a CAR which are also specific for the antigen CD142.

Example 6: Amino Acid Sequence of the CD73 Specific Antibody

The amino acid sequences of the variable portions of the immunoglobulin heavy chain and light chain of the used antibody specifically binding to CD73 were as given in SEQ ID NO:5 and SEQ ID NO:6, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD73 can be used to generate a CAR recognizing CD73. The sequences given in SEQ ID NO:5 and SEQ ID NO:6 are only exemplary for sequences which are specific for the antigen CD73 (the sequences are given in one letter code for amino acids). Other sequences may be used for generating antigen binding domains of an antibody or of a CAR which are also specific for the antigen CD73.

Example 7: Amino Acid Sequence of the CD49c Specific Antibody

The amino acid sequences of the variable portions of the immunoglobulin heavy chain and light chain of the used antibody specifically binding to CD49c were as given in SEQ ID NO:7 and SEQ ID NO:8, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD49c can be used to generate a CAR recognizing CD49c. The sequences given in SEQ ID NO:7 and SEQ ID NO:8 are only exemplary for sequences which are specific for the antigen CD49c (the sequences are given in one letter code for amino acids). Other sequences may be used for generating antigen binding domains of an antibody or of a CAR which are also specific for the antigen CD49c.

Example 8: Amino Acid Sequence of the CD66c Specific Antibody

The amino acid sequences of the variable portions of the immunoglobulin heavy chain and light chain of the used antibody specifically binding to CD66c were as given in SEQ ID NO:9 and SEQ ID NO:10, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD66c can be used to generate a CAR recognizing CD66c. The sequences given in SEQ ID NO:9 and SEQ ID NO:10 are only exemplary for sequences which are specific for the antigen CD66c (the sequences are given in one letter code for amino acids). Other sequences may be used for generating antigen binding domains of an antibody or of a CAR which are also specific for the antigen CD66c.

Example 9: Amino Acid Sequence of the CD104 Specific Antibody

The amino acid sequences of the variable portions of the immunoglobulin heavy chain and light chain of the used antibody specifically binding to CD104 were as given in SEQ ID NO: 11 and SEQ ID NO: 12, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD104 can be used to generate a CAR recognizing CD104. The sequences given in SEQ ID NO: 11 and SEQ ID NO: 12 are only exemplary for sequences which are specific for the antigen CD104 (the sequences are given in one letter code for amino acids). Other sequences may be used for generating antigen binding domains of an antibody or of a CAR which are also specific for the antigen CD104.

Example 10: Amino Acid Sequence of the CD318 Specific Antibody

The amino acid sequences of the variable portions of the immunoglobulin heavy chain and light chain of the used antibody specifically binding to CD318 were as given in SEQ ID NO: 13 and SEQ ID NO: 14, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for CD318 can be used to generate a CAR recognizing CD318. The sequences given in SEQ ID NO: 13 and SEQ ID NO: 14 are only exemplary for sequences which are specific for the antigen CD318 (the sequences are given in one letter code for amino acids). Other sequences may be used for generating antigen binding domains of an antibody or of a CAR which are also specific for the antigen CD318.

Example 11: Amino Acid Sequence of the TSPAN8 Specific Antibody

The amino acid sequences of the variable portions of the immunoglobulin heavy chain and light chain of the used antibody specifically binding to TSPAN8 were as given in SEQ ID NO: 15 and SEQ ID NO: 16, respectively. The relevant sites causing specificity for antigen binding are the CDRs according to the IMGT (the international ImMunoGeneTics information system for immunoglobulins or antibodies) definition which are underlined in the sequence. These sequences or any sequences derived thereof with a specificity for TSPAN8 can be used to generate a CAR recognizing TSPAN8. The sequences given in SEQ ID NO:15 and SEQ ID NO:16 are only exemplary for sequences which are specific for the antigen TSPAN8 (the sequences are given in one letter code for amino acids). Other sequences may be used for generating antigen binding domains of an antibody or of a CAR which are also specific for the antigen TSPAN8.

Figure 6:
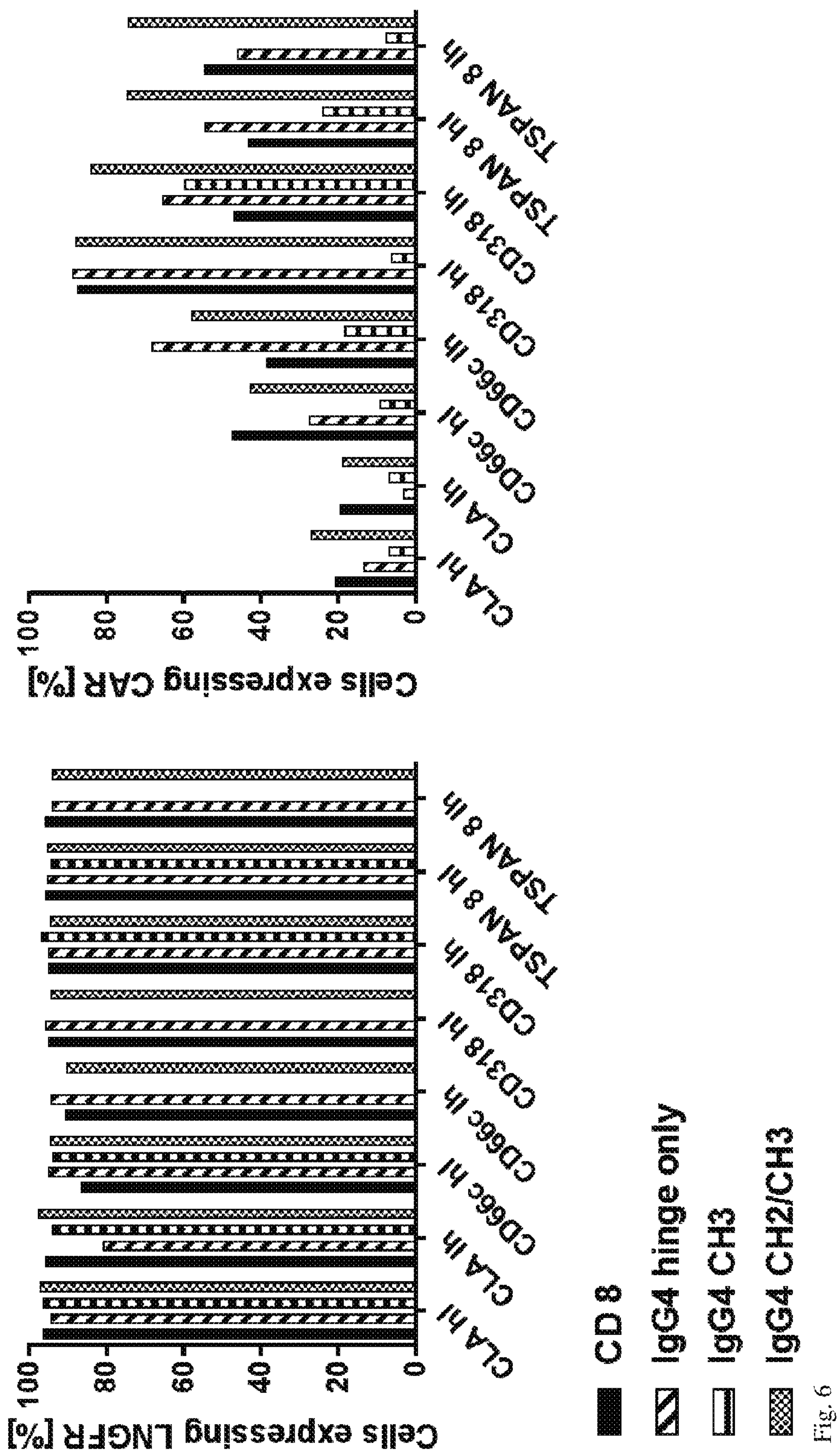
FIG. 6 shows the percentage of cells expressing LNGFR on the surface as a readout of transfection efficacy and construct expression and the percentage of cells expressing the CAR construct on the surface.

Example 12: Validation of CAR Expression 75.000 HEK 293T cells were inoculated in an 48-well. Cells were transfected with 0.5 μg plasmid using the MACSfectin transfection protocol 24 h later. Cells were detached 48 h post transfection using PBS supplemented with 1 mM EDTA. One third of the cells transfected with one plasmid was stained with an Anti-CD271 antibody (Miltenyi Biotec GmbH) following the recommended protocol. Another third was incubated 30 min at 4° C. with an Anti-Mouse IgG (Fab specific) antibody produced in goat (Sigma Aldrich) with 10 μg/ml antibody concentration. After a washing step cells were incubated with an Anti-Goat IgG (H+L) Cross-Adsorbed Secondary Antibody produced in chicken (Thermo Fisher Scientific) for 30 min at 4° C. with 10 μg/ml antibody concentration. The last third was stained solely as described with the secondary antibody as a background control. Samples were measured using a MACSQuant 10 analyzer. FIG. 6A shows the percentage of cells expressing LNGFR on the surface as a readout of transfection efficacy and construct expression. FIG. 6B shows the percentage of cells expressing the CAR construct on the surface. With few exceptions, all CAR molecules could be successfully expressed.

Example 13: Generation of Lentiviral Expression Vectors

The pancreas cancer specific CARs were cloned into third generation SIN-lentiviral vector constructs under the control of the human PGK promoter. Transient transfection of HEK 293T cells with this expression plasmid and further plasmids encoding the structural proteins gag-pol, rev and VSV-G envelope protein resulted in the release of viral vector particles into the supernatant. The viral vector particles were subsequently enriched by low speed centrifugation and stored at −70° C.

Example 14: T Cell Separation and Genetic Modification with Pancreas Cancer Specific CARs Primary T cells were isolated from donor apheresis or buffy coat samples using MicroBeads and MACS Technology® (Miltenyi Biotec GmbH, Germany) to reach purities of over 90% (CD3+ cells). Magnetically enriched cells were washed and resuspended in TexMACS medium supplemented with 200 IU/mL human recombinant IL-2 (Miltenyi Biotec GmbH, Germany). The T cells were then stimulated by addition of the GMP TransAct CD3/CD28 Reagent (Miltenyi Biotec GmbH, Germany).

After 24 hours, successful T cell stimulation was confirmed by staining the T cells with CD25 and CD69 antibodies and analysis by flow cytometry in a MACSQuant Analyzer (Miltenyi Biotec GmbH, Germany). The stimulated T cells were then transduced by adding lentiviral vectors encoding pancreas cancer specific CARs at an MOI=0.5-2. After 4 days of static culture the cells were washed to remove excess viral vector and TransAct Reagent and were cultivated for a further 5-10 days. The efficiency of viral transduction was measured by staining the surface expression of pancreas cancer specific CARs among live CD3+ cells using anti-human Fc fluorochrome and flow cytometry. The number of gene marked T cells ranged between 10 and 60%, depending on the MOI used.

Example 15: Pancreas Cancer Specific CARs Functionality

Cells expressing one or more of the pancreas cancer specific targets or cells not expressing these targets were incubated for 5 or 24 hours with expanded T cells expressing pancreas cancer specific CARs or, as a control, with non-transduced T cells at varied effector to target cell ratios. Specific target cell killing was analyzed by flow cytometry. Alternatively, the effector cells were restimulated with cell lines which were target-positive or -negative. Cytokine production (IFN-γ, IL-2, TNF-α) as well as degranulation (CD107a) were analyzed by flow cytometry. Only T cells carrying the pancreas cancer specific CARs were able to kill the target cells, showed increased cytokine production as well as degranulation marker upregulation.

Figure 7:
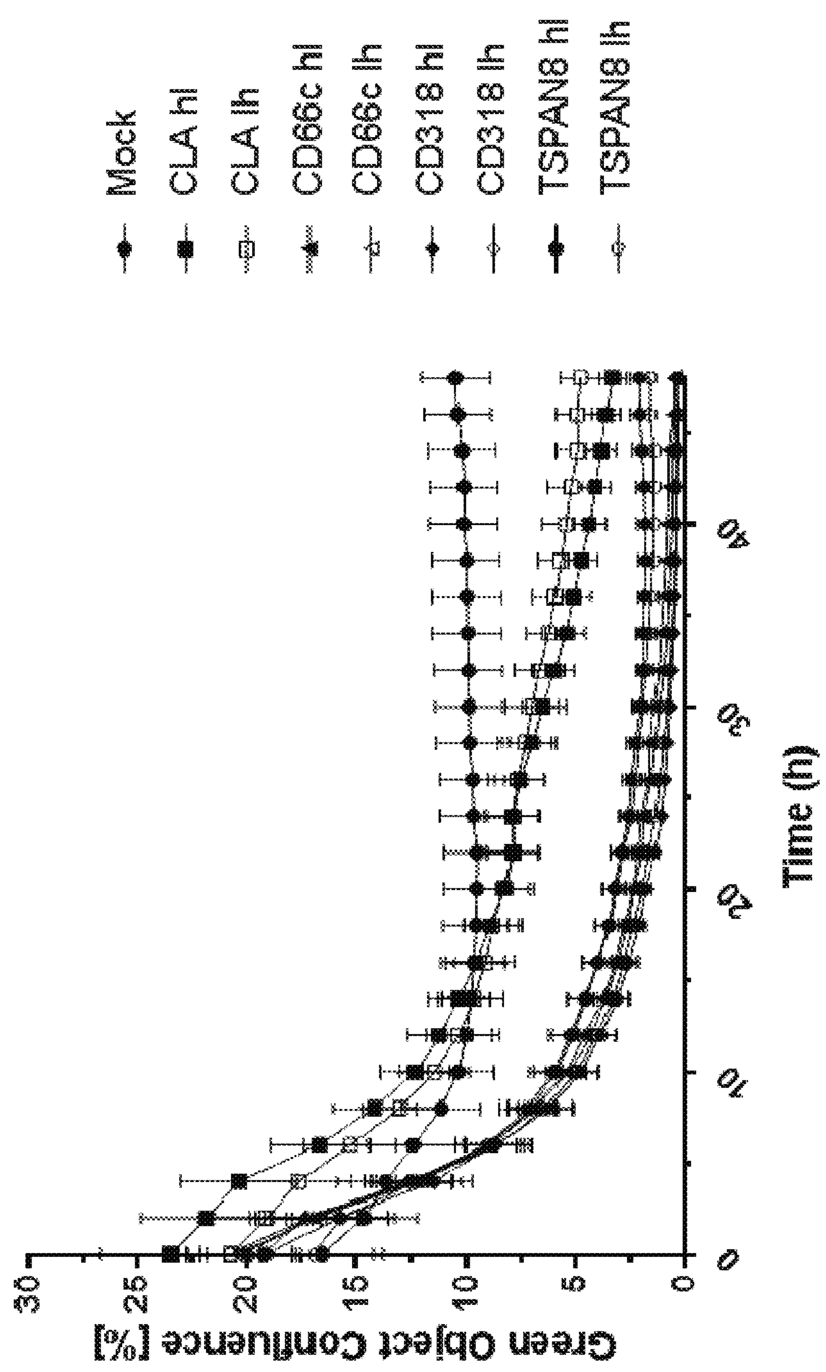
FIG. 7 shown the killing efficacy of CAR T cells towards pancreatic cancer cells.

Furthermore, the killing efficacy and kinetics were analyzed by long-term co-culture of CAR T cells and pancreatic cancer cells. T cells were isolated from a whole blood donation of a healthy donor using the Pan T Cell Isolation Kit (Miltenyi Biotec, Germany). Isolated T cells were activated in TexMACS™ GMP medium (Miltenyi Biotec, Germany) supplemented with 40 IU/ml IL-2 (Miltenyi Biotec, Germany) using MACS GMP T Cell TransAct (Miltenyi Biotec, Germany). After 24 h T cells were transduced with lentiviral vectors containing the CAR constructs at an MOI of 2. Subsequently, T cells were cultivated in TexMACS™ GMP medium supplemented with 40 IU/ml IL-2. On day 12 post transduction CAR expression was assessed via flow cytometric measurement of the reporter protein LNGFR. CAR positive T cells were adjusted to same numbers and inoculated in 96 well plates with pancreatic adenocarcinoma cell line BxPC3 in 200 μl TexMACS® GMP medium. Prior to this assay, BxPC3 cells were transduced with lentiviral vectors containing GFP. GFP positive cells were tracked and analyzed using the IncuCyte S3 (Essen BioScience, Germany). The "Green Object confluence" was used as a read out as it inversely correlates with the specific lysis of GFP expressing adherent target cells. All CAR constructs mediated efficient killing of tumor cells as compared to the mock control. Results are shown in FIG. 7.

Example 16: Amino Acid Sequences of CAR Binding Domains Recognizing CLA

For the antigen binding domain of a CAR specifically recognizing CLA, scFv's were used having the amino acid sequences of either SEQ ID NO: 17 or SEQ ID NO:18 (the sequences are given in one letter code of amino acids).

Example 17: Amino Acid Sequences of CAR Binding Domains Recognizing CD142

For the antigen binding domain of a CAR specifically recognizing CD142, scFv's were used having the amino acid sequences of either SEQ ID NO:19 or SEQ ID NO:20 (the sequences are given in one letter code of amino acids).

Example 18: Amino Acid Sequences of CAR Binding Domains Recognizing CD73

For the antigen binding domain of a CAR specifically recognizing CD73, scFv's were used having the amino acid sequences of either SEQ ID NO:21 or SEQ ID NO:22 (the sequences are given in one letter code of amino acids).

Example 19: Amino Acid Sequences of CAR Binding Domains Recognizing CD49c

For the antigen binding domain of a CAR specifically recognizing CD49c, scFv's were used having the amino acid sequences of either SEQ ID NO:23 or SEQ ID NO:24 (the sequences are given in one letter code of amino acids).

Example 20: Amino Acid Sequences of CAR Binding Domains Recognizing CD66c

For the antigen binding domain of a CAR specifically recognizing CD66c, scFv's were used having the amino acid sequences of either SEQ ID NO:25 or SEQ ID NO:26 (the sequences are given in one letter code of amino acids).

Example 21: Amino Acid Sequences of CAR Binding Domains Recognizing CD104

For the antigen binding domain of a CAR specifically recognizing CD104, scFv's were used having the amino acid sequences of either SEQ ID NO:27 or SEQ ID NO:28 (the sequences are given in one letter code of amino acids).

Example 22: Amino Acid Sequences of CAR Binding Domains Recognizing CD318

For the antigen binding domain of a CAR specifically recognizing CD318, scFv's were used having the amino acid sequences of either SEQ ID NO:29 or SEQ ID NO:30 (the sequences are given in one letter code of amino acids).

Example 23: Amino Acid Sequences of CAR Binding Domains Recognizing TSPAN8

For the antigen binding domain of a CAR specifically recognizing TSPAN8, scFv's were used having the amino acid sequences of either SEQ ID NO:31 or SEQ ID NO:32 (the sequences are given in one letter code of amino acids).

Figure 8A:
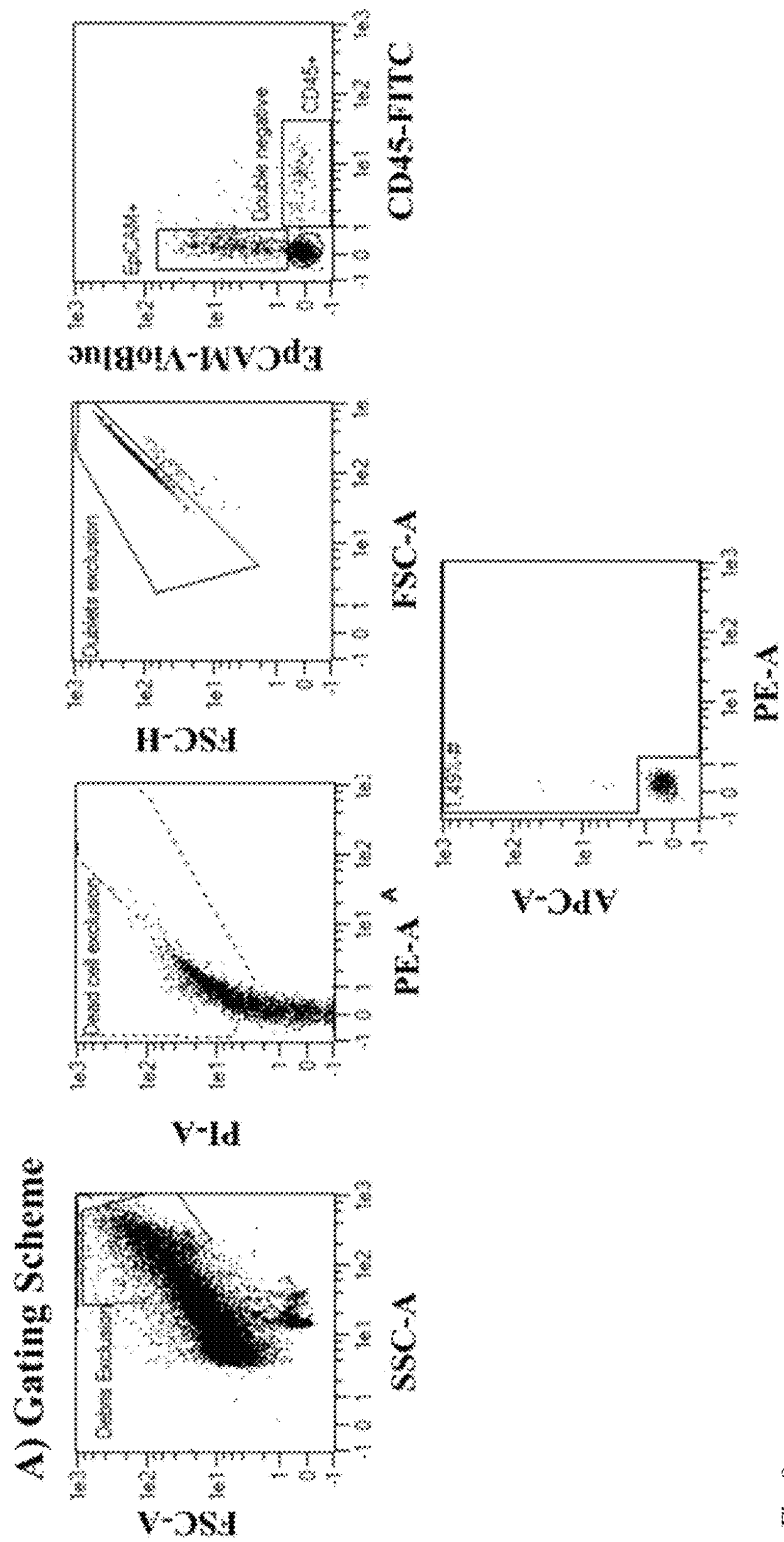
FIG. 8 A shows the gating and FIG. 8 B shows the co-expression of the markers.
Figure 8B:
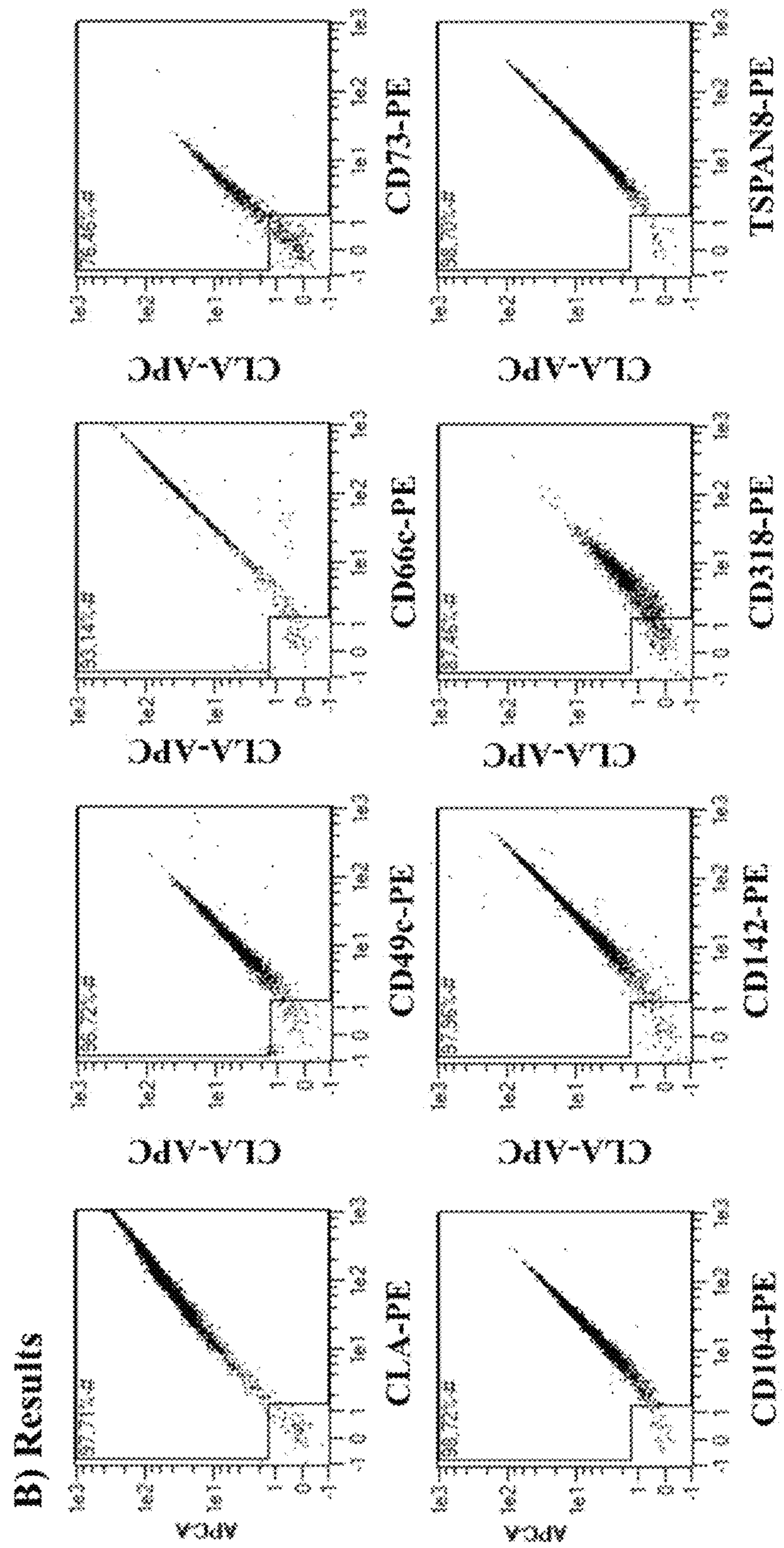

Example 24: Co-Expression of CLA and CD142, CD73, CD49c, CD66c, CD104, CD318 and TSPAN8 on Primary Human Pancreatic Cancer Cells Human pancreas adenocarcinoma tissue was dissociated, stained and analyzed. FIG. 6A shows the general gating strategy: after debris exclusion dead cells were excluded with a propidium iodide staining. Unwanted doublets were excluded by plotting the height against the area for forward scatter. EpCAM+, CD45+ as well as CD45−/EpCAM− cells were discriminated and further analyzed with PE or APC conjugated antibodies specific for the targets. FIG. 6B shows co-expression of CLA and CD142, CD73, CD49c, CD66c, CD104, CD318 and TSPAN8 on primary human pancreatic cancer cells. The results indicate a strong co-expression among these markers which is a pre-requisite for dual targeting (FIGS. 8A and B).

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

| Sequences |
|---|
| SEQ ID NO: 1<br>CLA $V_H$<br>EVQLVESGGGLVQPGNSLKLSCSASGFTFSSYGMHWIRQAPGEGLDWVAYISSSSGTVYADAVKARFTISRDNAKNTLYLQLNSLKSEDTAIYYCARAQNWDLFDYWGQGVMVTVSS |

-continued

Sequences

SEQ ID NO: 2
CLA $V_L$
QIMLTQQAESLWISPGERVSITCRASQSLLYTDGKHYLSWYQQKPGQTTK
ALIYHASVRTDGVPTRFIGSGSGTEFTLSIEHVQPEDFAIYYCLQTLKSP
FTFGSGTKLEIK

SEQ ID NO: 3
CD142 $V_H$
QVQLKQSGPGLVQPSQSLSITCTVSGFSLSNYGVHWVRQSPGKGLEWLGV
IWSGGSTDYNVAFISRLIITKDNSKSQVFLKMNSLQADDTAIYFCARTTG
SVFNAMDHWGQGTSVTVSS

SEQ ID NO: 4
CD142 $V_L$
QIVLTQSPALMSASPGEKVTMTCSASSSVTYMYWYQQKPRSSPKPWIYLT
SNLASGVPARFSGSGSGTSYSLTISSVEAEDAATYYCQQWSSNPLTFGAG
TKLELK

SEQ ID NO: 5
CD73 $V_H$
EVQLQQSGAELVKPGASVKLSCTASGFNIKDTYIHWVKQRPEQGLEWIGR
IDPATGNTEYDPKFQGKATITADTSSNTAYLHLSSLTSEDTAVYYCARGY
YGSSYPPWFAYWGQGTLVTVSA

SEQ ID NO: 6
CD73 $V_L$
DIVMTQSHKFMSTSVGDRVSITCKASQDVGSAVAWYQQKPGQSPKLLIYW
ASTRHTGVPDRFTGSGSGTDFTLTISNVQSEDLADYFCQQYSSYPLTFGA
GTKLELK

SEQ ID NO: 7
CD49c $V_H$
EVQLQQSGAELVKPGASVKLSCTASGFNIKDTYMHWVKQRPEQGLEWIGR
IDPANGHTKYDPKFQGKATITADTSSNAAYLQLNSLTSEDTAVYYCARRV
AYAMDYWGQGTSVTVSS

SEQ ID NO: 8
CD49c $V_L$
ENVLTQSPAIMSASPGEKVTMTCSASSSVTYMHWYQQKSSTSPKLWIYDT
SKLASGVPGRFSGSGSGNSYSLTISSMEAEDVATYCCFQGSGYPLTFGGG
TKLEIK

SEQ ID NO: 9
CD66c $V_H$
QVTLKESGPGILKPSQTLSLTCSFSGFSLSTSGMGVGWIRQPSGKSLEWL
AHIWWNDERYYNPSLKNQLTISKDTSRNQVFLKITSVDTADTATYYCARS
PRGYFDYWGHGTTLTVSS

SEQ ID NO: 10
CD66c $V_L$
DIVMTQSQKFMSTSVGDRVSVTCKASQNVVTNVAWYQQTPGQSPKALIYS
ASYRYSGVPDRFSGSGSGTDFTLTISNVQSGDLAEYFCQQYNSYPLTFGA
GTKLELK

SEQ ID NO: 11
CD104 $V_H$
QVNLLQSGAALVKPGASVKLSCKASGYTFTDYYIFWVKQSHGKSLEWIGY
INPNSGSTNYNEKFKRKATLSVDKSTNTAYMELSRLTSEDSATYYCTRRA
YYGYNPFDYWGQGVMVTVSS

SEQ ID NO: 12
CD104 $V_L$
DIQMTQTPSSMPASLGERVTISCRASRGINNYLSWYQQNLDGTIKPLIYY
TSNLQSGVPSRFSGSGSGTDYSLTISSLEPEDFAMYYCQQYDSSPWTFGG
GTKLELK

SEQ ID NO: 13
CD318 $V_H$
EVQLQQSGAELVRPGALVKLSCKASGFNIKDYYIHWVKQRPEQGLEWIGW
IDPENGHTIYDPKFQGKASITADTSSNTAYLQLSSLTSEDTAVYYCARLT
GTTYAMDYWGQGTSVTVSS

SEQ ID NO: 14
CD318 $V_L$
DIVMTQSHKFMSTSVGDRVSITCKASQDVSTAVAWYQQKSGQSPKLLIYW
ASTRHTGVPDRFTGSGSGTDYTLTISSVQAEDLALYYCQQHYSTPYTFGG
GTKLEIK

-continued

Sequences

SEQ ID NO: 15
TSPAN8 $V_H$
EVKLLESGGGLVQPGGSMRLSCAASGFTFTDFYMNWIRQPAGKAPEWLGF
IRNKASGYTTEYNPSVKGRFTISRDNTQNMLYLQMNTLRAEDTATYYCAR
AHSYYGYDYFDYWGQGVMVTVSS

SEQ ID NO: 16
TSPAN8 $V_L$
DIQMTQSPASLSASLEEIVTITCQASQDIGNWLSWYQQKPGKSPQLLIYG
ATSLADGVPSRFSGSRSGTQYSLKISRLQVEDIRIYYCLQAYSAPWTFGG
GTKLELK

SEQ ID NO: 17
CLA specific scFv VH-linker-VL
EVQLVESGGGLVQPGNSLKLSCSASGFTFSSYGMHWIRQAPGEGLDWVAY
ISSSSGTVYADAVKARFTISRDNAKNTLYLQLNSLKSEDTAIYYCARAQN
WDLFDYWGQGVMVTVSSGGGGSGGGGSGGGGSQIMLTQQAESLWISPGER
VSITCRASQSLLYTDGKHYLSWYQQKPGQTTKALIYHASVRTDGVPTRFI
GSGSGTEFTLSIEHVQPEDFAIYYCLQTLKSPFTFGSGTKLEIK SEQ ID NO: 18
CLA specific scFv VL-linker-VH
QIMLTQQAESLWISPGERVSITCRASQSLLYTDGKHYLSWYQQKPGQTTK
ALIYHASVRTDGVPTRFIGSGSGTEFTLSIEHVQPEDFAIYYCLQTLKSP
FTFGSGTKLEIKGGGGSGGGGSGGGGSEVQLVESGGGLVQPGNSLKLSCS
ASGFTFSSYGMHWIRQAPGEGLDWVAYISSSSGTVYADAVKARFTISRDN
AKNTLYLQLNSLKSEDTAIYYCARAQNWDLFDYWGQGVMVTVSS SEQ ID NO: 19
CD142 specific CAR sequence VH-linker-VL
QVQLKQSGPGLVQPSQSLSITCTVSGFSLSNYGVHWVRQSPGKGLEWLGV
IWSGGSTDYNVAFISRLIITKDNSKSQVFLKMNSLQADDTAIYFCARTTG
SVFNAMDHWGQGTSVTVSSGGGGSGGGGSGGGGSQIVLTQSPALMSASPG
EKVTMTCSASSSVTYMYWYQQKPRSSPKPWIYLTSNLASGVPARFSGSGS
GTSYSLTISSVEAEDAATYYCQQWSSNPLTFGAGTKLELK SEQ ID NO: 20
CD142 specific CAR sequence VL-linker-VH
QIVLTQSPALMSASPGEKVTMTCSASSSVTYMYWYQQKPRSSPKPWIYLT
SNLASGVPARFSGSGSGTSYSLTISSVEAEDAATYYCQQWSSNPLTFGAG
TKLELKGGGGSGGGGSGGGGSQVQLKQSGPGLVQPSQSLSITCTVSGFSL
SNYGVHWVRQSPGKGLEWLGVIWSGGSTDYNVAFISRLIITKDNSKSQVF
LKMNSLQADDTAIYFCARTTGSVFNAMDHWGQGTSVTVSS SEQ ID NO: 21
CD73 specific CAR sequence VH-linker-VL
EVQLQQSGAELVKPGASVKLSCTASGFNIKDTYIHWVKQRPEQGLEWIGR
IDPATGNTEYDPKFQGKATITADTSSNTAYLHLSSLTSEDTAVYYCARGY
YGSSYPPWFAYWGQGTLVTVSAGGGGSGGGGSGGGGSDIVMTQSHKFMST
SVGDRVSITCKASQDVGSAVAWYQQKPGQSPKLLIYWASTRHTGVPDRFT
GSGSGTDFTLTISNVQSEDLADYFCQQYSSYPLTFGAGTKLELK SEQ ID NO: 22
CD73 specific CAR sequence VL-linker-VH
DIVMTQSHKFMSTSVGDRVSITCKASQDVGSAVAWYQQKPGQSPKLLIYW
ASTRHTGVPDRFTGSGSGTDFTLTISNVQSEDLADYFCQQYSSYPLTFGA
GTKLELKGGGGSGGGGSGGGGSEVQLQQSGAELVKPGASVKLSCTASGFN
IKDTYIHWVKQRPEQGLEWIGRIDPATGNTEYDPKFQGKATITADTSSNT
AYLHLSSLTSEDTAVYYCARGYYGSSYPPWFAYWGQGTLVTVSA SEQ ID NO: 23
CD49c specific CAR sequence VH-linker-VL
EVQLQQSGAELVKPGASVKLSCTASGFNIKDTYMHWVKQRPEQGLEWIGR
IDPANGHTKYDPKFQGKATITADTSSNAAYLQLNSLTSEDTAVYYCARRV
AYAMDYWGQGTSVTVSSGGGGSGGGGSGGGGSENVLTQSPAIMSASPGEK
VTMTCSASSSVTYMHWYQQKSSTSPKLWIYDTSKLASGVPGRFSGSGSGN
SYSLTISSMEAEDVATYCCFQGSGYPLTFGGGTKLEIK SEQ ID NO: 24
CD49c specific CAR sequence VL-linker-VH
ENVLTQSPAIMSASPGEKVTMTCSASSSVTYMHWYQQKSSTSPKLWIYDT
SKLASGVPGRFSGSGSGNSYSLTISSMEAEDVATYCCFQGSGYPLTFGGG
TKLEIKGGGGSGGGGSGGGGSEVQLQQSGAELVKPGASVKLSCTASGFNI
KDTYMHWVKQRPEQGLEWIGRIDPANGHTKYDPKFQGKATITADTSSNAA
YLQLNSLTSEDTAVYYCARRVAYAMDYWGQGTSVTVSS -continued

| Sequences |
| --- |
| SEQ ID NO: 25<br>CD66c specific CAR sequence VH-linker-VL<br>QVTLKESGPGILKPSQTLSLTCSFSGFSLSTSGMGVGWIRQPSGKSLEWL<br>AHIWWNDERYYNPSLKNQLTISKDTSRNQVFLKITSVDTADTATYYCARS<br>PRGYFDYWGHGTTLTVSSGGGGSGGGGSGGGGSDIVMTQSQKFMSTSVGD<br>RVSVTCKASQNVVTNVAWYQQTPGQSPKALIYSASYRYSGVPDRFSGSGS<br>GTDFTLTISNVQSGDLAEYFCQQYNSYPLTFGAGTKLELK |
| SEQ ID NO: 26<br>CD66c specific CAR sequence VL-linker-VH<br>DIVMTQSQKFMSTSVGDRVSVTCKASQNVVTNVAWYQQTPGQSPKALIYS<br>ASYRYSGVPDRFSGSGSGTDFTLTISNVQSGDLAEYFCQQYNSYPLTFGA<br>GTKLELKGGGGSGGGGSGGGGSQVTLKESGPGILKPSQTLSLTCSFSGFS<br>LSTSGMGVGWIRQPSGKSLEWLAHIWWNDERYYNPSLKNQLTISKDTSRN<br>QVFLKITSVDTADTATYYCARSPRGYFDYWGHGTTLTVSS |
| SEQ ID NO: 27<br>CD104 specific CAR sequence VH-linker-VL<br>QVNLLQSGAALVKPGASVKLSCKASGYTFTDYYIFWVKQSHGKSLEWIGY<br>INPNSGSTNYNEKFKRKATLSVDKSTNTAYMELSRLTSEDSATYYCTRRA<br>YYGYNPFDYWGQGVMVTVSSGGGGSGGGGSGGGGSDIQMTQTPSSMPASL<br>GERVTISCRASRGINNYLSWYQQNLDGTIKPLIYYTSNLQSGVPSRFSGS<br>GSGTDYSLTISSLEPEDFAMYYCQQYDSSPWTFGGGTKLELK |
| SEQ ID NO: 28<br>CD104 specific CAR sequence VL-linker-VH<br>DIQMTQTPSSMPASLGERVTISCRASRGINNYLSWYQQNLDGTIKPLIYY<br>TSNLQSGVPSRFSGSGSGTDYSLTISSLEPEDFAMYYCQQYDSSPWTFGG<br>GTKLELKGGGGSGGGGSGGGGSQVNLLQSGAALVKPGASVKLSCKASGYT<br>FTDYYIFWVKQSHGKSLEWIGYINPNSGSTNYNEKFKRKATLSVDKSTNT<br>AYMELSRLTSEDSATYYCTRRAYYGYNPFDYWGQGVMVTVSS |

-continued

| Sequences |
| --- |
| SEQ ID NO: 29<br>CD318 specific CAR sequence VH-linker-VL<br>EVQLQQSGAELVRPGALVKLSCKASGFNIKDYYIHWVKQRPEQGLEWIGW<br>IDPENGHTIYDPKFQGKASITADTSSNTAYLQLSSLTSEDTAVYYCARLT<br>GTTYAMDYWGQGTSVTVSSGGGGSGGGGSGGGGSDIVMTQSHKFMSTSVG<br>DRVSITCKASQDVSTAVAWYQQKSGQSPKLLIYWASTRHTGVPDRFTGSG<br>SGTDYTLTISSVQAEDLALYYCQQHYSTPYTFGGGTKLEIK |
| SEQ ID NO: 30<br>CD318 specific CAR sequence VL-linker-VH<br>DIVMTQSHKFMSTSVGDRVSITCKASQDVSTAVAWYQQKSGQSPKLLIYW<br>ASTRHTGVPDRFTGSGSGTDYTLTISSVQAEDLALYYCQQHYSTPYTFGG<br>GTKLEIKGGGGSGGGGSGGGGSEVQLQQSGAELVRPGALVKLSCKASGFN<br>IKDYYIHWVKQRPEQGLEWIGWIDPENGHTIYDPKFQGKASITADTSSNT<br>AYLQLSSLTSEDTAVYYCARLTGTTYAMDYWGQGTSVTVSS |
| SEQ ID NO: 31<br>TSPAN8 specific CAR sequence VH-linker-VL<br>EVKLLESGGGLVQPGGSMRLSCAASGFTFTDFYMNWIRQPAGKAPEWLGF<br>IRNKASGYTTEYNPSVKGRFTISRDNTQNMLYLQMNTLRAEDTATYYCAR<br>AHSYYGYDYFDYWGQGVMVTVSSGGGGSGGGGSGGGGSDIQMTQSPASLS<br>ASLEEIVTITCQASQDIGNWLSWYQQKPGKSPQLLIYGATSLADGVPSRF<br>SGSRSGTQYSLKISRLQVEDIRIYYCLQAYSAPWTFGGGTKLELK |
| SEQ ID NO: 32<br>TSPAN8 specific CAR sequence VL-linker-VH<br>DIQMTQSPASLSASLEEIVTITCQASQDIGNWLSWYQQKPGKSPQLLIYG<br>ATSLADGVPSRFSGSRSGTQYSLKISRLQVEDIRIYYCLQAYSAPWTFGG<br>GTKLELKGGGGSGGGGSGGGGSEVKLLESGGGLVQPGGSMRLSCAASGFT<br>FTDFYMNWIRQPAGKAPEWLGFIRNKASGYTTEYNPSVKGRFTISRDNTQ<br>NMLYLQMNTLRAEDTATYYCARAHSYYGYDYFDYWGQGVMVTVSS |

What is claimed is:

1. A chimeric antigen receptor (CAR), comprising a first antigen binding domain specific for CD318 and a second antigen binding domain specific for an antigen selected from the group consisting of CD142, CD49c, and CD104, wherein the first and second antigen binding domains are conjugated to the same or a different transmembrane domain and/or intracellular signaling domain.

2. The chimeric antigen receptor (CAR) according to claim 1, characterized in that the same or different transmembrane domain comprises the transmembrane domain of one or more of 4-1BB, CD8 and/or CD28 and the intracellular signaling domain comprises the intracellular signaling domains of one or more of CD28, CD137 and CD3zeta.

* * * * *

SEQUENCE LISTING

```
<160> NUMBER OF SEQ ID NOS: 32

<210> SEQ ID NO 1
<211> LENGTH: 117
<212> TYPE: PRT
<213> ORGANISM: Homo sapiens
<220> FEATURE:
<223> OTHER INFORMATION: CLA VH

<400> SEQUENCE: 1

Glu Val Gln Leu Val Glu Ser Gly Gly Gly Leu Val Gln Pro Gly Asn
1               5                   10                  15

Ser Leu Lys Leu Ser Cys Ser Ala Ser Gly Phe Thr Phe Ser Ser Tyr
            20                  25                  30

Gly Met His Trp Ile Arg Gln Ala Pro Gly Glu Gly Leu Asp Trp Val
        35                  40                  45

Ala Tyr Ile Ser Ser Ser Ser Gly Thr Val Tyr Ala Asp Ala Val Lys
    50                  55                  60

Ala Arg Phe Thr Ile Ser Arg Asp Asn Ala Lys Asn Thr Leu Tyr Leu
65                  70                  75                  80

Gln Leu Asn Ser Leu Lys Ser Glu Asp Thr Ala Ile Tyr Tyr Cys Ala
                85                  90                  95

Arg Ala Gln Asn Trp Asp Leu Phe Asp Tyr Trp Gly Gln Gly Val Met
            100                 105                 110

Val Thr Val Ser Ser
        115


<210> SEQ ID NO 2
<211> LENGTH: 112
<212> TYPE: PRT
```

```
<213> ORGANISM: Homo sapiens
<220> FEATURE:
<223> OTHER INFORMATION: CLA VL

<400> SEQUENCE: 2

Gln Ile Met Leu Thr Gln Gln Ala Glu Ser Leu Trp Ile Ser Pro Gly
1               5                   10                  15

Glu Arg Val Ser Ile Thr Cys Arg Ala Ser Gln Ser Leu Leu Tyr Thr
            20                  25                  30

Asp Gly Lys His Tyr Leu Ser Trp Tyr Gln Gln Lys Pro Gly Gln Thr
        35                  40                  45

Thr Lys Ala Leu Ile Tyr His Ala Ser Val Arg Thr Asp Gly Val Pro
    50                  55                  60

Thr Arg Phe Ile Gly Ser Gly Ser Gly Thr Glu Phe Thr Leu Ser Ile
65                  70                  75                  80

Glu His Val Gln Pro Glu Asp Phe Ala Ile Tyr Tyr Cys Leu Gln Thr
                85                  90                  95

Leu Lys Ser Pro Phe Thr Phe Gly Ser Gly Thr Lys Leu Glu Ile Lys
            100                 105                 110


<210> SEQ ID NO 3
<211> LENGTH: 119
<212> TYPE: PRT
<213> ORGANISM: Homo sapiens
<220> FEATURE:
<223> OTHER INFORMATION: CD142 VH

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Val Ala Phe Ile
    50                  55                  60

Ser Arg Leu Ile Ile Thr Lys Asp Asn Ser Lys Ser Gln Val Phe Leu
65                  70                  75                  80

Lys Met Asn Ser Leu Gln Ala Asp Asp Thr Ala Ile Tyr Phe Cys Ala
                85                  90                  95

Arg Thr Thr Gly Ser Val Phe Asn Ala Met Asp His Trp Gly Gln Gly
            100                 105                 110

Thr Ser Val Thr Val Ser Ser
        115


<210> SEQ ID NO 4
<211> LENGTH: 106
<212> TYPE: PRT
<213> ORGANISM: Homo sapiens
<220> FEATURE:
<223> OTHER INFORMATION: CD142 VL

<400> SEQUENCE: 4

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
        35                  40                  45
```

```
Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105


<210> SEQ ID NO 5
<211> LENGTH: 122
<212> TYPE: PRT
<213> ORGANISM: Homo sapiens
<220> FEATURE:
<223> OTHER INFORMATION: CD73 VH

<400> SEQUENCE: 5

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Thr Gly Asn Thr Glu Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Gly Tyr Tyr Gly Ser Ser Tyr Pro Pro Trp Phe Ala Tyr Trp
            100                 105                 110

Gly Gln Gly Thr Leu Val Thr Val Ser Ala
        115                 120


<210> SEQ ID NO 6
<211> LENGTH: 107
<212> TYPE: PRT
<213> ORGANISM: Homo sapiens
<220> FEATURE:
<223> OTHER INFORMATION: CD73 VL

<400> SEQUENCE: 6

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105
```

-continued

```
<210> SEQ ID NO 7
<211> LENGTH: 117
<212> TYPE: PRT
<213> ORGANISM: Homo sapiens
<220> FEATURE:
<223> OTHER INFORMATION: CD49C VH

<400> SEQUENCE: 7

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly His Thr Lys Tyr Asp Pro Lys Phe
    50                  55                  60

Gln Gly Lys Ala Thr Ile Thr Ala Asp Thr Ser Ser Asn Ala Ala Tyr
65                  70                  75                  80

Leu Gln Leu Asn Ser Leu Thr Ser Glu Asp Thr Ala Val Tyr Tyr Cys
                85                  90                  95

Ala Arg Arg Val Ala Tyr Ala Met Asp Tyr Trp Gly Gln Gly Thr Ser
            100                 105                 110

Val Thr Val Ser Ser
        115


<210> SEQ ID NO 8
<211> LENGTH: 106
<212> TYPE: PRT
<213> ORGANISM: Homo sapiens
<220> FEATURE:
<223> OTHER INFORMATION: CD49C VL

<400> SEQUENCE: 8

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Cys Cys Phe Gln Gly Ser Gly Tyr Pro Leu Thr
                85                  90                  95

Phe Gly Gly Gly Thr Lys Leu Glu Ile Lys
            100                 105


<210> SEQ ID NO 9
<211> LENGTH: 118
<212> TYPE: PRT
<213> ORGANISM: Homo sapiens
<220> FEATURE:
<223> OTHER INFORMATION: CD66C VH

<400> SEQUENCE: 9

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30
```

```
Gly Met Gly Val Gly Trp Ile Arg Gln Pro Ser Gly Lys Ser Leu Glu
        35                  40                  45

Trp Leu Ala His Ile Trp Trp Asn Asp Glu Arg Tyr Tyr Asn Pro Ser
    50                  55                  60

Leu Lys Asn Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Pro Arg Gly Tyr Phe Asp Tyr Trp Gly His Gly Thr
            100                 105                 110

Thr Leu Thr Val Ser Ser
        115


<210> SEQ ID NO 10
<211> LENGTH: 107
<212> TYPE: PRT
<213> ORGANISM: Homo sapiens
<220> FEATURE:
<223> OTHER INFORMATION: CD66C VL

<400> SEQUENCE: 10

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Val Thr Asn
            20                  25                  30

Val Ala Trp Tyr Gln Gln Thr Pro Gly Gln Ser Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Gly Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105


<210> SEQ ID NO 11
<211> LENGTH: 120
<212> TYPE: PRT
<213> ORGANISM: Homo sapiens
<220> FEATURE:
<223> OTHER INFORMATION: CD104 VH

<400> SEQUENCE: 11

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile Phe Trp Val Lys Gln Ser His Gly Lys Ser Leu Glu Trp Ile
        35                  40                  45

Gly Tyr Ile Asn Pro Asn Ser Gly Ser Thr Asn Tyr Asn Glu Lys Phe
    50                  55                  60

Lys Arg Lys Ala Thr Leu Ser Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95
```

```
Thr Arg Arg Ala Tyr Tyr Gly Tyr Asn Pro Phe Asp Tyr Trp Gly Gln
            100                 105                 110

Gly Val Met Val Thr Val Ser Ser
        115                 120


<210> SEQ ID NO 12
<211> LENGTH: 107
<212> TYPE: PRT
<213> ORGANISM: Homo sapiens
<220> FEATURE:
<223> OTHER INFORMATION: CD104 VL

<400> SEQUENCE: 12

Asp Ile Gln Met Thr Gln Thr Pro Ser Ser Met Pro Ala Ser Leu Gly
1               5                   10                  15

Glu Arg Val Thr Ile Ser Cys Arg Ala Ser Arg Gly Ile Asn Asn Tyr
            20                  25                  30

Leu Ser Trp Tyr Gln Gln Asn Leu Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Trp
                85                  90                  95

Thr Phe Gly Gly Gly Thr Lys Leu Glu Leu Lys
            100                 105


<210> SEQ ID NO 13
<211> LENGTH: 119
<212> TYPE: PRT
<213> ORGANISM: Homo sapiens
<220> FEATURE:
<223> OTHER INFORMATION: CD318 VH

<400> SEQUENCE: 13

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly His Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Leu Thr Gly Thr Thr Tyr Ala Met Asp Tyr Trp Gly Gln Gly
            100                 105                 110

Thr Ser Val Thr Val Ser Ser
        115


<210> SEQ ID NO 14
<211> LENGTH: 107
<212> TYPE: PRT
<213> ORGANISM: Homo sapiens
<220> FEATURE:
<223> OTHER INFORMATION: CD318 VL
```

<400> SEQUENCE: 14

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Ser Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105
```

<210> SEQ ID NO 15
<211> LENGTH: 123
<212> TYPE: PRT
<213> ORGANISM: Homo sapiens
<220> FEATURE:
<223> OTHER INFORMATION: TSPAN8 VH

<400> SEQUENCE: 15

```
Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asn Lys Ala Ser Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ala His Ser Tyr Tyr Gly Tyr Asp Tyr Phe Asp Tyr
            100                 105                 110

Trp Gly Gln Gly Val Met Val Thr Val Ser Ser
        115                 120
```

<210> SEQ ID NO 16
<211> LENGTH: 107
<212> TYPE: PRT
<213> ORGANISM: Homo sapiens
<220> FEATURE:
<223> OTHER INFORMATION: TSPAN8 VL

<400> SEQUENCE: 16

```
Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60
```

```
Ser Arg Ser Gly Thr Gln Tyr Ser Leu Lys Ile Ser Arg Leu Gln Val
65              70                  75                  80

Glu Asp Ile Arg Ile Tyr Tyr Cys Leu Gln Ala Tyr Ser Ala Pro Trp
                85                  90                  95

Thr Phe Gly Gly Gly Thr Lys Leu Glu Leu Lys
            100                 105


<210> SEQ ID NO 17
<211> LENGTH: 244
<212> TYPE: PRT
<213> ORGANISM: Homo sapiens
<220> FEATURE:
<223> OTHER INFORMATION: CLA SPECIFIC SCFV VH-LINKER-VL

<400> SEQUENCE: 17

Glu Val Gln Leu Val Glu Ser Gly Gly Gly Leu Val Gln Pro Gly Asn
1               5                   10                  15

Ser Leu Lys Leu Ser Cys Ser Ala Ser Gly Phe Thr Phe Ser Ser Tyr
            20                  25                  30

Gly Met His Trp Ile Arg Gln Ala Pro Gly Glu Gly Leu Asp Trp Val
        35                  40                  45

Ala Tyr Ile Ser Ser Ser Ser Gly Thr Val Tyr Ala Asp Ala Val Lys
    50                  55                  60

Ala Arg Phe Thr Ile Ser Arg Asp Asn Ala Lys Asn Thr Leu Tyr Leu
65                  70                  75                  80

Gln Leu Asn Ser Leu Lys Ser Glu Asp Thr Ala Ile Tyr Tyr Cys Ala
                85                  90                  95

Arg Ala Gln Asn Trp Asp Leu Phe Asp Tyr Trp Gly Gln Gly Val Met
            100                 105                 110

Val Thr Val Ser Ser Gly Gly Gly Gly Ser Gly Gly Gly Gly Ser Gly
        115                 120                 125

Gly Gly Gly Ser Gln Ile Met Leu Thr Gln Gln Ala Glu Ser Leu Trp
    130                 135                 140

Ile Ser Pro Gly Glu Arg Val Ser Ile Thr Cys Arg Ala Ser Gln Ser
145                 150                 155                 160

Leu Leu Tyr Thr Asp Gly Lys His Tyr Leu Ser Trp Tyr Gln Gln Lys
                165                 170                 175

Pro Gly Gln Thr Thr Lys Ala Leu Ile Tyr His Ala Ser Val Arg Thr
            180                 185                 190

Asp Gly Val Pro Thr Arg Phe Ile Gly Ser Gly Ser Gly Thr Glu Phe
        195                 200                 205

Thr Leu Ser Ile Glu His Val Gln Pro Glu Asp Phe Ala Ile Tyr Tyr
    210                 215                 220

Cys Leu Gln Thr Leu Lys Ser Pro Phe Thr Phe Gly Ser Gly Thr Lys
225                 230                 235                 240

Leu Glu Ile Lys


<210> SEQ ID NO 18
<211> LENGTH: 244
<212> TYPE: PRT
<213> ORGANISM: Homo sapiens
<220> FEATURE:
<223> OTHER INFORMATION: CLA SPECIFIC SCFV VL-LINKER-VH

<400> SEQUENCE: 18

Gln Ile Met Leu Thr Gln Gln Ala Glu Ser Leu Trp Ile Ser Pro Gly
1               5                   10                  15
```

```
Glu Arg Val Ser Ile Thr Cys Arg Ala Ser Gln Ser Leu Leu Tyr Thr
            20                  25                  30

Asp Gly Lys His Tyr Leu Ser Trp Tyr Gln Gln Lys Pro Gly Gln Thr
        35                  40                  45

Thr Lys Ala Leu Ile Tyr His Ala Ser Val Arg Thr Asp Gly Val Pro
    50                  55                  60

Thr Arg Phe Ile Gly Ser Gly Ser Gly Thr Glu Phe Thr Leu Ser Ile
65                  70                  75                  80

Glu His Val Gln Pro Glu Asp Phe Ala Ile Tyr Tyr Cys Leu Gln Thr
                85                  90                  95

Leu Lys Ser Pro Phe Thr Phe Gly Ser Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Gly Leu Val Gln Pro Gly Asn Ser
    130                 135                 140

Leu Lys Leu Ser Cys Ser Ala Ser Gly Phe Thr Phe Ser Ser Tyr Gly
145                 150                 155                 160

Met His Trp Ile Arg Gln Ala Pro Gly Glu Gly Leu Asp Trp Val Ala
                165                 170                 175

Tyr Ile Ser Ser Ser Ser Gly Thr Val Tyr Ala Asp Ala Val Lys Ala
            180                 185                 190

Arg Phe Thr Ile Ser Arg Asp Asn Ala Lys Asn Thr Leu Tyr Leu Gln
        195                 200                 205

Leu Asn Ser Leu Lys Ser Glu Asp Thr Ala Ile Tyr Tyr Cys Ala Arg
    210                 215                 220

Ala Gln Asn Trp Asp Leu Phe Asp Tyr Trp Gly Gln Gly Val Met Val
225                 230                 235                 240

Thr Val Ser Ser


<210> SEQ ID NO 19
<211> LENGTH: 240
<212> TYPE: PRT
<213> ORGANISM: Homo sapiens
<220> FEATURE:
<223> OTHER INFORMATION: CD142 SPECIFIC CAR SEQUENCE VH-LINKER-VL

<400> SEQUENCE: 19

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Val Ala Phe Ile
    50                  55                  60

Ser Arg Leu Ile Ile Thr Lys Asp Asn Ser Lys Ser Gln Val Phe Leu
65                  70                  75                  80

Lys Met Asn Ser Leu Gln Ala Asp Asp Thr Ala Ile Tyr Phe Cys Ala
                85                  90                  95

Arg Thr Thr Gly Ser Val Phe Asn Ala Met Asp His Trp Gly Gln Gly
            100                 105                 110

Thr Ser Val Thr Val Ser Ser Gly Gly Gly Gly Ser Gly Gly Gly Gly
        115                 120                 125
```

```
Ser Gly Gly Gly Gly Ser Gln Ile Val Leu Thr Gln Ser Pro Ala Leu
    130                 135                 140

Met Ser Ala Ser Pro Gly Glu Lys Val Thr Met Thr Cys Ser Ala Ser
145                 150                 155                 160

Ser Ser Val Thr Tyr Met Tyr Trp Tyr Gln Gln Lys Pro Arg Ser Ser
                165                 170                 175

Pro Lys Pro Trp Ile Tyr Leu Thr Ser Asn Leu Ala Ser Gly Val Pro
            180                 185                 190

Ala Arg Phe Ser Gly Ser Gly Ser Gly Thr Ser Tyr Ser Leu Thr Ile
        195                 200                 205

Ser Ser Val Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240


<210> SEQ ID NO 20
<211> LENGTH: 240
<212> TYPE: PRT
<213> ORGANISM: Homo sapiens
<220> FEATURE:
<223> OTHER INFORMATION: CD142 SPECIFIC CAR SEQUENCE VL-LINKER-VH

<400> SEQUENCE: 20

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Gln Val Gln Leu Lys Gln Ser
        115                 120                 125

Gly Pro Gly Leu Val Gln Pro Ser Gln Ser Leu Ser Ile Thr Cys Thr
    130                 135                 140

Val Ser Gly Phe Ser Leu Ser Asn Tyr Gly Val His Trp Val Arg Gln
145                 150                 155                 160

Ser Pro Gly Lys Gly Leu Glu Trp Leu Gly Val Ile Trp Ser Gly Gly
                165                 170                 175

Ser Thr Asp Tyr Asn Val Ala Phe Ile Ser Arg Leu Ile Ile Thr Lys
            180                 185                 190

Asp Asn Ser Lys Ser Gln Val Phe Leu Lys Met Asn Ser Leu Gln Ala
        195                 200                 205

Asp Asp Thr Ala Ile Tyr Phe Cys Ala Arg Thr Thr Gly Ser Val Phe
    210                 215                 220

Asn Ala Met Asp His Trp Gly Gln Gly Thr Ser Val Thr Val Ser Ser
225                 230                 235                 240


<210> SEQ ID NO 21
<211> LENGTH: 244
```

<212> TYPE: PRT
<213> ORGANISM: Homo sapiens
<220> FEATURE:
<223> OTHER INFORMATION: CD73 SPECIFIC CAR SEQUENCE VH-LINKER-VL

<400> SEQUENCE: 21

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Thr Gly Asn Thr Glu Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Gly Tyr Tyr Gly Ser Ser Tyr Pro Pro Trp Phe Ala Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Asp Ile Val Met Thr Gln Ser
    130                 135                 140

His Lys Phe Met Ser Thr Ser Val Gly Asp Arg Val Ser Ile Thr Cys
145                 150                 155                 160

Lys Ala Ser Gln Asp Val Gly Ser Ala Val Ala Trp Tyr Gln Gln Lys
                165                 170                 175

Pro Gly Gln Ser Pro Lys Leu Leu Ile Tyr Trp Ala Ser Thr Arg His
            180                 185                 190

Thr Gly Val Pro Asp Arg Phe Thr Gly Ser Gly Ser Gly Thr Asp Phe
        195                 200                 205

Thr Leu Thr Ile Ser Asn Val Gln Ser Glu Asp Leu Ala Asp Tyr Phe
    210                 215                 220

Cys Gln Gln Tyr Ser Ser Tyr Pro Leu Thr Phe Gly Ala Gly Thr Lys
225                 230                 235                 240

Leu Glu Leu Lys
```

<210> SEQ ID NO 22
<211> LENGTH: 244
<212> TYPE: PRT
<213> ORGANISM: Homo sapiens
<220> FEATURE:
<223> OTHER INFORMATION: CD73 SPECIFIC CAR SEQUENCE VL-LINKER-VH

<400> SEQUENCE: 22

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

```
Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Gly Ser Glu Val Gln Leu Gln Gln
        115                 120                 125

Ser Gly Ala Glu Leu Val Lys Pro Gly Ala Ser Val Lys Leu Ser Cys
    130                 135                 140

Thr Ala Ser Gly Phe Asn Ile Lys Asp Thr Tyr Ile His Trp Val Lys
145                 150                 155                 160

Gln Arg Pro Glu Gln Gly Leu Glu Trp Ile Gly Arg Ile Asp Pro Ala
                165                 170                 175

Thr Gly Asn Thr Glu Tyr Asp Pro Lys Phe Gln Gly Lys Ala Thr Ile
            180                 185                 190

Thr Ala Asp Thr Ser Ser Asn Thr Ala Tyr Leu His Leu Ser Ser Leu
        195                 200                 205

Thr Ser Glu Asp Thr Ala Val Tyr Tyr Cys Ala Arg Gly Tyr Tyr Gly
    210                 215                 220

Ser Ser Tyr Pro Pro Trp Phe Ala Tyr Trp Gly Gln Gly Thr Leu Val
225                 230                 235                 240

Thr Val Ser Ala


<210> SEQ ID NO 23
<211> LENGTH: 238
<212> TYPE: PRT
<213> ORGANISM: Homo sapiens
<220> FEATURE:
<223> OTHER INFORMATION: CD49C SPECIFIC CAR SEQUENCE VH-LINKER-VL

<400> SEQUENCE: 23

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly His Thr Lys Tyr Asp Pro Lys Phe
    50                  55                  60

Gln Gly Lys Ala Thr Ile Thr Ala Asp Thr Ser Ser Asn Ala Ala Tyr
65                  70                  75                  80

Leu Gln Leu Asn Ser Leu Thr Ser Glu Asp Thr Ala Val Tyr Tyr Cys
                85                  90                  95

Ala Arg Arg Val Ala Tyr Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Glu Asn Val Leu Thr Gln Ser Pro Ala Ile Met Ser
    130                 135                 140

Ala Ser Pro Gly Glu Lys Val Thr Met Thr Cys Ser Ala Ser Ser Ser
145                 150                 155                 160

Val Thr Tyr Met His Trp Tyr Gln Gln Lys Ser Ser Thr Ser Pro Lys
                165                 170                 175

Leu Trp Ile Tyr Asp Thr Ser Lys Leu Ala Ser Gly Val Pro Gly Arg
            180                 185                 190
```

```
Phe Ser Gly Ser Gly Ser Gly Asn Ser Tyr Ser Leu Thr Ile Ser Ser
        195                 200                 205

Met Glu Ala Glu Asp Val Ala Thr Tyr Cys Cys Phe Gln Gly Ser Gly
    210                 215                 220

Tyr Pro Leu Thr Phe Gly Gly Gly Thr Lys Leu Glu Ile Lys
225                 230                 235


<210> SEQ ID NO 24
<211> LENGTH: 238
<212> TYPE: PRT
<213> ORGANISM: Homo sapiens
<220> FEATURE:
<223> OTHER INFORMATION: CD49C SPECIFIC CAR SEQUENCE VL-LINKER-VH

<400> SEQUENCE: 24

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Cys Cys Phe Gln Gly Ser Gly Tyr Pro Leu Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Glu Val Gln Leu Gln Gln Ser
        115                 120                 125

Gly Ala Glu Leu Val Lys Pro Gly Ala Ser Val Lys Leu Ser Cys Thr
    130                 135                 140

Ala Ser Gly Phe Asn Ile Lys Asp Thr Tyr Met His Trp Val Lys Gln
145                 150                 155                 160

Arg Pro Glu Gln Gly Leu Glu Trp Ile Gly Arg Ile Asp Pro Ala Asn
                165                 170                 175

Gly His Thr Lys Tyr Asp Pro Lys Phe Gln Gly Lys Ala Thr Ile Thr
            180                 185                 190

Ala Asp Thr Ser Ser Asn Ala Ala Tyr Leu Gln Leu Asn Ser Leu Thr
        195                 200                 205

Ser Glu Asp Thr Ala Val Tyr Tyr Cys Ala Arg Arg Val Ala Tyr Ala
    210                 215                 220

Met Asp Tyr Trp Gly Gln Gly Thr Ser Val Thr Val Ser Ser
225                 230                 235


<210> SEQ ID NO 25
<211> LENGTH: 240
<212> TYPE: PRT
<213> ORGANISM: Homo sapiens
<220> FEATURE:
<223> OTHER INFORMATION: CD66C SPECIFIC CAR SEQUENCE VH-LINKER-VL

<400> SEQUENCE: 25

Gln Val Thr Leu Lys Glu Ser Gly Pro Gly Ile Leu Lys Pro Ser Gln
1               5                   10                  15
```

```
Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Ser Leu Glu
        35                  40                  45

Trp Leu Ala His Ile Trp Trp Asn Asp Glu Arg Tyr Tyr Asn Pro Ser
    50                  55                  60

Leu Lys Asn Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Pro Arg Gly Tyr Phe Asp Tyr Trp Gly His Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Gln Lys Phe Met
    130                 135                 140

Ser Thr Ser Val Gly Asp Arg Val Ser Val Thr Cys Lys Ala Ser Gln
145                 150                 155                 160

Asn Val Val Thr Asn Val Ala Trp Tyr Gln Gln Thr Pro Gly Gln Ser
                165                 170                 175

Pro Lys Ala Leu Ile Tyr Ser Ala Ser Tyr Arg Tyr Ser Gly Val Pro
            180                 185                 190

Asp Arg Phe Ser Gly Ser Gly Ser Gly Thr Asp Phe Thr Leu Thr Ile
        195                 200                 205

Ser Asn Val Gln Ser Gly Asp Leu Ala Glu Tyr Phe Cys Gln Gln Tyr
    210                 215                 220

Asn Ser Tyr Pro Leu Thr Phe Gly Ala Gly Thr Lys Leu Glu Leu Lys
225                 230                 235                 240
```

<210> SEQ ID NO 26
<211> LENGTH: 240
<212> TYPE: PRT
<213> ORGANISM: Homo sapiens
<220> FEATURE:
<223> OTHER INFORMATION: CD66C SPECIFIC CAR SEQUENCE VL-LINKER-VH

<400> SEQUENCE: 26

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Val Thr Asn
            20                  25                  30

Val Ala Trp Tyr Gln Gln Thr Pro Gly Gln Ser Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Gly Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Gly Ser Gln Val Thr Leu Lys Glu
        115                 120                 125

Ser Gly Pro Gly Ile Leu Lys Pro Ser Gln Thr Leu Ser Leu Thr Cys
    130                 135                 140
```

```
Ser Phe Ser Gly Phe Ser Leu Ser Thr Ser Gly Met Gly Val Gly Trp
145                 150                 155                 160

Ile Arg Gln Pro Ser Gly Lys Ser Leu Glu Trp Leu Ala His Ile Trp
                165                 170                 175

Trp Asn Asp Glu Arg Tyr Tyr Asn Pro Ser Leu Lys Asn Gln Leu Thr
            180                 185                 190

Ile Ser Lys Asp Thr Ser Arg Asn Gln Val Phe Leu Lys Ile Thr Ser
        195                 200                 205

Val Asp Thr Ala Asp Thr Ala Thr Tyr Tyr Cys Ala Arg Ser Pro Arg
    210                 215                 220

Gly Tyr Phe Asp Tyr Trp Gly His Gly Thr Thr Leu Thr Val Ser Ser
225                 230                 235                 240


<210> SEQ ID NO 27
<211> LENGTH: 242
<212> TYPE: PRT
<213> ORGANISM: Homo sapiens
<220> FEATURE:
<223> OTHER INFORMATION: CD104 SPECIFIC CAR SEQUENCE VH-LINKER-VL

<400> SEQUENCE: 27

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile Phe Trp Val Lys Gln Ser His Gly Lys Ser Leu Glu Trp Ile
        35                  40                  45

Gly Tyr Ile Asn Pro Asn Ser Gly Ser Thr Asn Tyr Asn Glu Lys Phe
    50                  55                  60

Lys Arg Lys Ala Thr Leu Ser Val Asp Lys Ser Thr Asn Thr Ala Tyr
65                  70                  75                  80

Met Glu Leu Ser Arg Leu Thr Ser Glu Asp Ser Ala Thr Tyr Tyr Cys
                85                  90                  95

Thr Arg Arg Ala Tyr Tyr Gly Tyr Asn Pro Phe Asp Tyr Trp Gly Gln
            100                 105                 110

Gly Val Met Val Thr Val Ser Ser Gly Gly Gly Gly Ser Gly Gly Gly
        115                 120                 125

Gly Ser Gly Gly Gly Gly Ser Asp Ile Gln Met Thr Gln Thr Pro Ser
    130                 135                 140

Ser Met Pro Ala Ser Leu Gly Glu Arg Val Thr Ile Ser Cys Arg Ala
145                 150                 155                 160

Ser Arg Gly Ile Asn Asn Tyr Leu Ser Trp Tyr Gln Gln Asn Leu Asp
                165                 170                 175

Gly Thr Ile Lys Pro Leu Ile Tyr Tyr Thr Ser Asn Leu Gln Ser Gly
            180                 185                 190

Val Pro Ser Arg Phe Ser Gly Ser Gly Ser Gly Thr Asp Tyr Ser Leu
        195                 200                 205

Thr Ile Ser Ser Leu Glu Pro Glu Asp Phe Ala Met Tyr Tyr Cys Gln
    210                 215                 220

Gln Tyr Asp Ser Ser Pro Trp Thr Phe Gly Gly Gly Thr Lys Leu Glu
225                 230                 235                 240

Leu Lys


<210> SEQ ID NO 28
<211> LENGTH: 242
```

```
<212> TYPE: PRT
<213> ORGANISM: Homo sapiens
<220> FEATURE:
<223> OTHER INFORMATION: CD104 SPECIFIC CAR SEQUENCE VL-LINKER-VH

<400> SEQUENCE: 28

Asp Ile Gln Met Thr Gln Thr Pro Ser Ser Met Pro Ala Ser Leu Gly
1               5                   10                  15

Glu Arg Val Thr Ile Ser Cys Arg Ala Ser Arg Gly Ile Asn Asn Tyr
            20                  25                  30

Leu Ser Trp Tyr Gln Gln Asn Leu Asp Gly Thr Ile Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Ser Ser Pro Trp
                85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Gly Ser Gln Val Asn Leu Leu Gln
        115                 120                 125

Ser Gly Ala Ala Leu Val Lys Pro Gly Ala Ser Val Lys Leu Ser Cys
    130                 135                 140

Lys Ala Ser Gly Tyr Thr Phe Thr Asp Tyr Tyr Ile Phe Trp Val Lys
145                 150                 155                 160

Gln Ser His Gly Lys Ser Leu Glu Trp Ile Gly Tyr Ile Asn Pro Asn
                165                 170                 175

Ser Gly Ser Thr Asn Tyr Asn Glu Lys Phe Lys Arg Lys Ala Thr Leu
            180                 185                 190

Ser Val Asp Lys Ser Thr Asn Thr Ala Tyr Met Glu Leu Ser Arg Leu
        195                 200                 205

Thr Ser Glu Asp Ser Ala Thr Tyr Tyr Cys Thr Arg Arg Ala Tyr Tyr
    210                 215                 220

Gly Tyr Asn Pro Phe Asp Tyr Trp Gly Gln Gly Val Met Val Thr Val
225                 230                 235                 240

Ser Ser


<210> SEQ ID NO 29
<211> LENGTH: 241
<212> TYPE: PRT
<213> ORGANISM: Homo sapiens
<220> FEATURE:
<223> OTHER INFORMATION: CD318 SPECIFIC CAR SEQUENCE VH-LINKER-VL

<400> SEQUENCE: 29

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly His Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80
```

```
Leu Gln Leu Ser Ser Leu Thr Ser Glu Asp Thr Ala Val Tyr Tyr Cys
                85                  90                  95

Ala Arg Leu Thr Gly Thr Thr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Val Met Thr Gln Ser His Lys Phe
    130                 135                 140

Met Ser Thr Ser Val Gly Asp Arg Val Ser Ile Thr Cys Lys Ala Ser
145                 150                 155                 160

Gln Asp Val Ser Thr Ala Val Ala Trp Tyr Gln Gln Lys Ser Gly Gln
                165                 170                 175

Ser Pro Lys Leu Leu Ile Tyr Trp Ala Ser Thr Arg His Thr Gly Val
            180                 185                 190

Pro Asp Arg Phe Thr Gly Ser Gly Ser Gly Thr Asp Tyr Thr Leu Thr
        195                 200                 205

Ile Ser Ser Val Gln Ala Glu Asp Leu Ala Leu Tyr Tyr Cys Gln Gln
    210                 215                 220

His Tyr Ser Thr Pro Tyr Thr Phe Gly Gly Gly Thr Lys Leu Glu Ile
225                 230                 235                 240

Lys


<210> SEQ ID NO 30
<211> LENGTH: 241
<212> TYPE: PRT
<213> ORGANISM: Homo sapiens
<220> FEATURE:
<223> OTHER INFORMATION: CD318 SPECIFIC CAR SEQUENCE VL-LINKER-VH

<400> SEQUENCE: 30

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Ser Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Glu Val Gln Leu Gln Gln
        115                 120                 125

Ser Gly Ala Glu Leu Val Arg Pro Gly Ala Leu Val Lys Leu Ser Cys
    130                 135                 140

Lys Ala Ser Gly Phe Asn Ile Lys Asp Tyr Tyr Ile His Trp Val Lys
145                 150                 155                 160

Gln Arg Pro Glu Gln Gly Leu Glu Trp Ile Gly Trp Ile Asp Pro Glu
                165                 170                 175

Asn Gly His Thr Ile Tyr Asp Pro Lys Phe Gln Gly Lys Ala Ser Ile
            180                 185                 190
```

```
Thr Ala Asp Thr Ser Ser Asn Thr Ala Tyr Leu Gln Leu Ser Ser Leu
        195                 200                 205

Thr Ser Glu Asp Thr Ala Val Tyr Tyr Cys Ala Arg Leu Thr Gly Thr
    210                 215                 220

Thr Tyr Ala Met Asp Tyr Trp Gly Gln Gly Thr Ser Val Thr Val Ser
225                 230                 235                 240

Ser
```

<210> SEQ ID NO 31
<211> LENGTH: 245
<212> TYPE: PRT
<213> ORGANISM: Homo sapiens
<220> FEATURE:
<223> OTHER INFORMATION: TSPAN8 SPECIFIC CAR SEQUENCE VH-LINKER-VL

<400> SEQUENCE: 31

```
Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asn Lys Ala Ser Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Ala His Ser Tyr Tyr Gly Tyr Asp Tyr Phe Asp Tyr
            100                 105                 110

Trp Gly Gln Gly Val Met Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ala Ser Leu Ser Ala Ser Leu Glu Glu Ile Val Thr Ile Thr
145                 150                 155                 160

Cys Gln Ala Ser Gln Asp Ile Gly Asn Trp Leu Ser Trp Tyr Gln Gln
                165                 170                 175

Lys Pro Gly Lys Ser Pro Gln Leu Leu Ile Tyr Gly Ala Thr Ser Leu
            180                 185                 190

Ala Asp Gly Val Pro Ser Arg Phe Ser Gly Ser Arg Ser Gly Thr Gln
        195                 200                 205

Tyr Ser Leu Lys Ile Ser Arg Leu Gln Val Glu Asp Ile Arg Ile Tyr
    210                 215                 220

Tyr Cys Leu Gln Ala Tyr Ser Ala Pro Trp Thr Phe Gly Gly Gly Thr
225                 230                 235                 240

Lys Leu Glu Leu Lys
                245
```

<210> SEQ ID NO 32
<211> LENGTH: 245
<212> TYPE: PRT
<213> ORGANISM: Homo sapiens
<220> FEATURE:
<223> OTHER INFORMATION: TSPAN8 SPECIFIC CAR SEQUENCE VL-LINKER-VH

```
<400> SEQUENCE: 32

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Arg Ile Tyr Tyr Cys Leu Gln Ala Tyr Ser Ala Pro Trp
                85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Gly Ser Glu Val Lys Leu Leu Glu
        115                 120                 125

Ser Gly Gly Gly Leu Val Gln Pro Gly Gly Ser Met Arg Leu Ser Cys
    130                 135                 140

Ala Ala Ser Gly Phe Thr Phe Thr Asp Phe Tyr Met Asn Trp Ile Arg
145                 150                 155                 160

Gln Pro Ala Gly Lys Ala Pro Glu Trp Leu Gly Phe Ile Arg Asn Lys
                165                 170                 175

Ala Ser Gly Tyr Thr Thr Glu Tyr Asn Pro Ser Val Lys Gly Arg Phe
            180                 185                 190

Thr Ile Ser Arg Asp Asn Thr Gln Asn Met Leu Tyr Leu Gln Met Asn
        195                 200                 205

Thr Leu Arg Ala Glu Asp Thr Ala Thr Tyr Tyr Cys Ala Arg Ala His
    210                 215                 220

Ser Tyr Tyr Gly Tyr Asp Tyr Phe Asp Tyr Trp Gly Gln Gly Val Met
225                 230                 235                 240

Val Thr Val Ser Ser
                245
```